(12) United States Patent
Strandberg et al.

(10) Patent No.: US 11,519,875 B2
(45) Date of Patent: Dec. 6, 2022

(54) SENSOR DEVICE, MEASURING SYSTEM AND MEASURING METHOD FOR DETECTING PRESENCE OF LIQUID AND/OR HUMIDITY

(71) Applicant: Invisense AB, Linköping (SE)

(72) Inventors: Jan Strandberg, Linköping (SE); Duncan Platt, Norrköping (SE)

(73) Assignee: Invisense AB, Linköping (SE)

( * ) Notice: Subject to any disclaimer, the term of this patent is extended or adjusted under 35 U.S.C. 154(b) by 534 days.

(21) Appl. No.: 16/487,312

(22) PCT Filed: Feb. 21, 2018

(86) PCT No.: PCT/EP2018/054215
§ 371 (c)(1),
(2) Date: Aug. 20, 2019

(87) PCT Pub. No.: WO2018/153885
PCT Pub. Date: Aug. 30, 2018

(65) Prior Publication Data
US 2020/0057014 A1 Feb. 20, 2020

(30) Foreign Application Priority Data

Feb. 21, 2017 (SE) .................................. 1750182-6
Feb. 21, 2017 (SE) .................................. 1750183-4

(51) Int. Cl.
*G01N 27/22* (2006.01)
*G01N 33/00* (2006.01)
*G01K 7/34* (2006.01)

(52) U.S. Cl.
CPC ............. *G01N 27/225* (2013.01); *G01K 7/34* (2013.01); *G01N 27/223* (2013.01); *G01N 33/0032* (2013.01)

(58) Field of Classification Search
CPC .. G01N 27/225; G01N 27/223; G01N 27/121; G01N 27/22; G01N 27/227;
(Continued)

(56) References Cited

U.S. PATENT DOCUMENTS 5,283,711 A * 2/1994 Schmitz ............... G01N 27/225
73/335.04
2006/0176152 A1 8/2006 Wagner et al.
(Continued)

FOREIGN PATENT DOCUMENTS

EP 2275805 A1 * 1/2011 ........... G01N 27/223
EP 2275806 A2 * 1/2011 ........... G01N 27/223
(Continued)

OTHER PUBLICATIONS

International Search Report for International Application No. PCT/EP2018/054215, dated Jun. 1, 2018 (3 pages).

*Primary Examiner* — Nimeshkumar D Patel
*Assistant Examiner* — Gedeon M Kidanu
(74) *Attorney, Agent, or Firm* — Kagan Binder, PLLC

(57) ABSTRACT

The present invention relates to a sensor device (10) for detection of liquid and/or humidity. The sensor device comprises a resonance circuit comprising an inductor (13) connected to a capacitor (11), wherein the capacitor comprises a first electrode (11a) and a second electrode (11b) together sandwiching at least a portion of a dielectric substrate (14). The first and second electrodes are configured to provide an overlap mismatch relative to each other, and the overlap mismatch area (ma) is at least 0.1% of the overlapping area ($o_a$) of the two electrodes. The present invention further relates to a system (70) for reading a sensor device and a method (100, 200) for reading a sensor device.

16 Claims, 11 Drawing Sheets

(58) Field of Classification Search
CPC .............. G01N 27/228; G01N 27/407; G01N 33/0032; G01K 7/16; G01K 7/203; H01L 2223/6677; H01L 2224/16225; H01L 23/34; H01L 23/5223; H01L 23/5227; H01L 23/5228; H01L 23/5329; H01L 23/66; H01L 27/105; H01L 27/15; H01L 2924/00; H01L 2924/1305
See application file for complete search history.

(56) References Cited

U.S. PATENT DOCUMENTS

| | | | |
|---|---|---|---|
| 2011/0011179 A1* | 1/2011 | Gustafsson | G01N 27/223 |
| | | | 73/335.03 |
| 2011/0241835 A1* | 10/2011 | Amtman | G06K 7/0008 |
| | | | 340/10.1 |
| 2012/0304742 A1 | 12/2012 | Cummins | |
| 2016/0161435 A1 | 6/2016 | Fujimoto et al. | |
| 2016/0363555 A1* | 12/2016 | Kang | G01N 27/407 |
| 2018/0113533 A1* | 4/2018 | Shinoda | G06F 3/044 |

FOREIGN PATENT DOCUMENTS

| | | | |
|---|---|---|---|
| EP | 2275806 B1 | 1/2011 | |
| WO | WO-03081232 A1 * | 10/2003 | ............. F01M 11/10 |

\* cited by examiner

SENSOR DEVICE, MEASURING SYSTEM AND MEASURING METHOD FOR DETECTING PRESENCE OF LIQUID AND/OR HUMIDITY

CROSS-REFERENCE TO RELATED APPLICATIONS

This application claims priority to International Application No. PCT/EP2018/054215, filed Feb. 21, 2018 and titled "SENSOR DEVICE, MEASURING SYSTEM AND MEASURING METHOD FOR DETECTING PRESENCE OF LIQUID AND/OR HUMIDITY," which in turn claims priority from a Swedish Application having serial number 1750183-4, flied Feb. 21, 2017, titled "SENSOR DEVICE, MEASURING SYSTEM AND MEASURING METHOD FOR DETECTING PRESENCE OF LIQUID AND/OR HUMIDITY" and from a Swedish Application having serial number 1750182-6, filed Feb. 21, 2017, titled "SENSOR DEVICE, MEASURING SYSTEM AND MEASURING METHOD FOR DETECTING PRESENCE OF LIQUID AND/OR HUMIDITY," both of which are incorporated herein by reference in their entireties

TECHNICAL FIELD

The present disclosure relates to a sensor and measuring method for detecting presence of liquid, especially wireless interrogation of a liquid and/or humidity sensor.

BACKGROUND

There are situations, where it is desirable to detect the presence of a liquid and/or humidity in a structure without having to breach a surface of the structure. Examples of such situations may be where glue, or compounds for fixing or leveling, has been applied under an exposed surface covering, which is impermeable to the liquid. This would be the case when a water based glue is used to apply a vinyl covering for a wall or a floor.

In such situations, it may be desirable to be able to verify that e.g. the solvent (which may, but need not, be water) in the glue is being properly absorbed by the underlying material. If this is not happening, then it may be necessary to tear away the covering and reapply it. Naturally, the impermeable nature of the covering makes it impossible to electrically measure the presence of the solvent under the covering.

A further example may be the need to detect the presence of humidity in a building structure, after the construction thereof is finished. Such detection may be desired years after the completion to determine the condition of the structure. However, to access the interior of the structure to electrically measure the humidity therein the exposed surface of the building structure will need to be opened in a destructive way, requiring a costly restoration thereafter.

One known technology for detecting moisture is disclosed in EP2275806B1. However, the hygroscopic electrolyte used in such sensor has severe drawbacks in providing an accurate detection of liquid and/or humidity. The electrolyte's reaction to moisture or water may be unpredictable in certain conditions, thereby making the detection unreliable.

Hence, there is a need for a method which allows non-destructive and reliable detection of the presence of liquid and/or humidity in a structure.

SUMMARY

It is an object of the present invention to provide a solution for detection of the presence of a liquid and/or humidity in a structure that is non-destructive to the structure. The invention is defined by the appended independent claims, with embodiments being set forth in the appended dependent claims, in the following description and in the drawings.

According to a first aspect of the invention, a sensor device for detection of liquid and/or humidity is provided. The sensor device comprises a resonance circuit comprising an inductor connected to a capacitor, wherein the capacitor comprises a first electrode and a second electrode together sandwiching at least a portion of a dielectric substrate. The first and second electrodes are configured to provide an overlap mismatch relative to each other, and the overlap mismatch area is at least 0.1% of the overlapping area of the two electrodes.

The sensor device may be provided to be read by a measuring unit. The resonance circuit may be configured to respond to an interrogation signal from the measuring unit, providing an inductive coupling with the measuring unit. The response signal may be induced in the resonance circuit by the interrogation signal. The properties of the response signal depend on the characteristics of the resonance circuit. For instance, the properties of the response signal may depend on the capacitance value of the capacitor and on the inductance value of the inductor. Hence, the design of the resonance circuit will determine its response characteristics. Design of resonance circuits is known as such to the skilled person.

When two electrodes in a capacitor are placed with a mismatch, intentionally or unintentionally, parasitic capacitances, or stray capacitances, may occur when the capacitor is powered. The invention is based on the recognition that the resulting capacitance value of the capacitor may increase when a solvent, and in particular a polar solvent, such as water, is present around the sensor device. The dielectric constant of air is in the order of 1, and most solid materials have a dielectric constant in the order of 3-5. Water on the other hand has a dielectric constant in the order of 80. Hence, when water is present around the sensor device, the parasitic capacitances will greatly increase.

This effect may be used by intentionally providing an overlap mismatch area between the first and second electrodes and may be detected by interrogating the sensor device by measuring a resonance response signal of the circuit in the sensor device. The parasitic capacitances may affect the value of the capacitor and thereby affect the resonance frequency of the resonance LC circuit. The resonance frequency of the LC circuit may be provided by the inverse of the square root of (L*C). The LC circuit may be tuned to resonate at a frequency of about 4-15 MHz, preferably of about 7-9.5 MHz, and most preferably of about 7.1-9.1 MHz. The level of parasitic capacitances may make the resonance frequency of the circuit to differ within said interval. The frequency of a response signal provided by the sensor device when receiving an interrogation signal may thereby be used for detecting the presence of a liquid at the sensor device's location.

The overlapping area may be of the size of the common area of the substrate along which both the first and the second electrode extends on the respective opposite sides of the substrate. The mismatch area may be the sum of the parts of the first electrode's and the second electrode's respective extension areas minus the overlap area. I.e. the area of the substrate on which either of the electrodes extend without a corresponding other electrode extending to the same area on the opposite side of the substrate. In an exemplary embodiment, one of the electrodes may have a size of 35*18 mm.

The other electrode may have a size of 34.5*17.5 mm, such that the larger electrode may extend 0.25 mm outside the extension of the smaller electrode an all four sides thereof. The overlap area may thereby be 603.75 mm$^2$, and the mismatch area may be 26.25 mm$^2$, equal to 4.3% of the overlap area. Both larger and smaller mismatch area relative to the overlap area may be suitable. For instance, the greater electrode may extend outside the overlap area in only one direction by 0.25 mm. The mismatch area may thereby be 0.7% of the overlap area. With larger electrodes a larger overlap area may be provided, for instance 65*65 mm, and such mismatch extension of 0.25 mm in one direction may provide a mismatch area of 0.4%.

A mismatch area of at least 0.1% of the overlap area may be desired. In one embodiment preferably at least 0.5%. In another embodiment preferably at least 1%. In a further embodiment at least 2%. In a yet further embodiment at least 3%.

Further, the mismatch area may in one embodiment be less than 20% of the overlap area. In another embodiment less than 15%. A mismatch area of less than 20% or 15% may provide a necessary amount of parasitic capacitances, without them having too large impact on the resulting capacitance, and without negatively affecting the function of the capacitor.

In one embodiment, one of the first and second electrodes may provide a greater electrode area than the other of the electrodes.

In order to intentionally introduce a certain amount of parasitic capacitances, the electrodes may be placed with an intended overlap mismatch. Such mismatch may be provided by one of the electrodes being larger, i.e. having a greater electrode area, than the other one of the electrodes. A desired amount of mismatch may thereby be secured. The larger electrode may be either the first electrode being on the same face side of the substrate as the inductor, or the second electrode arranged on the opposite second face side of the substrate.

In a further embodiment, the electrode providing a greater electrode area may extend in a plane in parallel with the other one of the two electrodes, and said electrode with greater electrode area may have a greater extent in at least one direction in said plane than the other of the electrodes.

The electrode that may provide a greater electrode area may provide a greater extension in only one direction along the plane. Alternatively, the larger electrode may provide a greater extension in a plurality of directions in said plane. The extension of the larger electrode may be designed to provide a desired amount of parasitic capacitances.

In another embodiment, the first electrode may be formed on a first face side of the dielectric substrate, and the inductor may be formed as a planar inductor on said first face side of the dielectric substrate.

The sensor device may be formed of the dielectric substrate with the first electrode and the inductor formed on the first face side of the dielectric substrate and the second electrode formed on a second face side of the dielectric substrate, said second face side being opposite said first face side. The inductor may be in electrical connection with the first electrode. The electrodes and the inductor may be printed on the substrate. The first electrode and the inductor may be formed of a common material on the first face side.

In one embodiment, the connection between the inductor and the second electrode of the capacitor may be provided by a connection element.

The connection element may provide a connection between the inductor being formed on the first face side of the substrate and the second electrode being formed on the second face side. The connection element may provide a connection through the substrate.

In a further embodiment, the connection element may comprise a resistive element or a capacitive element.

Said capacitor may be a first capacitor, and the connection element in the form of a capacitive element may be provided as a second capacitor. The second capacitor may be formed of a third electrode and a fourth electrode. The third electrode may be formed on the first face side of the substrate. The fourth electrode may be formed on the second face side of the substrate. The third electrode may be in electrical connection with the inductor. The fourth electrode may be in electrical connection with the second electrode of the first capacitor. The second capacitor may preferably be arranged with an overlap mismatch in the same way as the first capacitor. Hence, the overlap mismatch area between the third and fourth electrodes of the second capacitor may be at least 0.1% of the overlap area, in one embodiment preferably at least 0.5% and in another embodiment preferably at least 1%. In a further embodiment the mismatch area may be at least 2% of the overlap area. In a yet further embodiment at least 3%. Further, the mismatch area may in one embodiment be less than 20% of the overlap area. In another embodiment less than 15%. In one exemplary embodiment, one of the electrodes in the second capacitor may have an area of 60*10 mm, and the other of the electrodes may have an area of 59.5*9.5 mm, such that the larger electrodes extends by 0.25 mm outside the smaller electrode's extension on all four sides thereof. The overlap area may thereby be 565.25 mm$^2$, and the mismatch area 34.75 mm$^2$, providing the mismatch area to be 5.8% of the overlap area.

By providing a second capacitor, the electrical connection between inductor and the first capacitor may be provided in suitable arrangement on the respective face sides of the substrate. A first end of the inductor may be connected to the first electrode of the first capacitor, and the second capacitor may provide a connection from a second end of the inductor arranged on the first face side of the substrate to the second opposite face side of the substrate and further to the second electrode of the first capacitor.

The connection element may further be provided as a resistive element extending through the substrate from a first face side of the substrate to a second opposite face side of the substrate. The resistive element may be connected to the inductor on the first face side and to the second electrode on the second face side.

The resistive element may be formed of a first connector member on the first face side of the substrate, and a second connector member on the second face side of the substrate, wherein one of the connector members extends through the substrate to be in direct connection with the other one of the two connector members. The connection element may be formed as a resistive element extending through the substrate. The two connector members may be formed of separate materials. In a preferred embodiment, the second connector member may be arranged to extend through the substrate. In one embodiment, the connection element may be formed by first arranging the first connector member on the first face side of the substrate. Next a hole through the substrate may be provided at the location of the first connector member, but which hole may not extend through the first connector member. Such hole may be provided by means of e.g. laser etching. Next, the second connector member may be formed by arranging a material therefore on the second face side of the substrate, wherein said material may further fill the hole.

Alternatively, the resistive element may be provided as an element formed of a single material extending from the first face side to the second face side through said hole in the substrate.

When using a resistive element as the connection element, the size of the first capacitor may be reduced since a more effective electrical connection between the components of the resonance circuit may be provided.

In one embodiment, the first electrode may comprise a metal layer.

The first electrode may be provided on the substrate as a metal layer. The metal layer may be a patterned metal film. All components on the first face side of the substrate may be formed of the same material, i.e. the first electrode and the inductor. In an embodiment wherein a second capacitor is provided, also the third electrode of the second capacitor arranged on the first face side may be formed of said material. In an embodiment wherein a resistive element is provided, also a portion of the resistive element, such as a connector member, arranged on the first face side of the substrate may be formed of the same material.

In one embodiment, the first electrode is formed of Aluminum or Copper. Other conducting materials may alternatively be used.

The first electrode, as well as optionally other components on the first face side of the substrate, may alternatively be formed by printing of an electrically conductive ink or polymer.

In a further embodiment, the second electrode may comprise an electrically conductive ink or polymer.

The electrically conductive ink or polymer may for instance be a silver containing ink, a conducting polymer or graphene. The electrically conductive ink or polymer may have been printed on the substrate, for instance by screen printing. A second electrode formed of an electrically conductive ink or polymer may provide an electrode being liquid permeable in order to enable liquid and/or humidity to reach the substrate between the electrodes. All components on a first face side of the substrate may be formed of the same material. In an embodiment wherein a second capacitor is provided, also the fourth electrode of the second capacitor arranged on the second face side of the substrate may be formed of the electrically conductive ink or polymer. In an embodiment wherein a connection element is provided, also a connector member of the connection element arranged on the second face side of the substrate may be formed of the electrically conductive ink or polymer. Further, the connector member of the connection element extending through the substrate may be formed of the electrically conductive ink or polymer.

In one embodiment, the dielectric substrate may comprise a homogeneous material having a dielectric constant which is variable in response to liquid and/or humidity in its environment.

By homogeneous it may be meant a material devoid of pockets of liquid or gas. The dielectric constant of the substrate may affect the capacitance value of the capacitor. The substrate material may be configured to absorb liquid and/or humidity in its environment. Such liquid/humidity may provide water or moisture of the humidity of the environment of the sensor device. Hence, the capacitance value of the capacitor may vary depending on the surrounding humidity of the sensor device. The amount of liquid and/or humidity that may be absorbed by the substrate may be linear to the presence of liquid and/or humidity. When absorbing the liquid and/or humidity, the substrate's dielectric constant may change. More absorbed particles may provide an increased dielectric constant. An increased dielectric constant may provide an increased capacitance value of the capacitor, and thereby a decreased resonance frequency of the circuit. By using a substrate that has a dielectric constant which may vary in response to the presence of liquid and/or humidity, not only will the parasitic capacitance in the circuit vary, but also the capacitance value of the capacitor due to dielectric constant of the substrate. It may thereby not only be possible to detect the presence of liquid or humidity by means of the parasitic capacitance, but also to measure the relative humidity of the surrounding by means of the substrate's dielectric constant. This may especially be important when the content of liquid around the sensor device has been reduced to such extent that there is no free liquid in the environment, but humidity of the surroundings.

In a further embodiment, the dielectric substrate material may be configured to absorb liquid and/or humidity, and the material may retain its dimensions +/−0.1%, preferably +/−0.01%, after a complete absorption-desorption cycle.

The dielectric substrate material may be configured to retain its physical dimensions after a complete absorption-desorption cycle. By such cycle it may be meant that the substrate in a first process absorbs liquid and/or humidity in the environment at the sensor device up to a value, and in a second process desorbs the corresponding amount of liquid and/or humidity. The dielectric constant of the substrate may thereby be substantially the same prior the absorption-desorption cycle as after. By retaining its physical dimensions, it may be meant a retention of its dimensions +/−0.1%, preferably +/−0.01%. The capacitance value of the capacitor may thereby not be affected by any change in dimensions of the substrate over time.

In a yet further embodiment, the dielectric substrate may comprise at least 70% by weight of a polymer selected from a group consisting of polyimides and polyethylene-tetrafluorides.

A substrate comprising polyimide or polyethylene-tetrafluoride may provide a suitable liquid and/or humidity absorption capacity without significant dimensional change, while at the same time provide a varying dielectric constant in response to liquid and/or humidity in its environment. Optionally, the substrate may consist essentially of said polymer. Further, optionally, the substrate may consist of said polymer.

In one embodiment, the dielectric substrate may have a thickness less than 2 mm, preferably less than 1 mm, and more preferably less than 0.5 mm.

In another embodiment, at least one of the first electrode and the second electrode may be liquid permeable.

In order to detect the presence of liquid and/or humidity in the environment of the sensor device, the liquid and/or humidity may need to get in contact with the substrate. To facilitate such process, at least one of the electrodes may be liquid permeable. By being liquid permeable it may be meant that the electrode is formed such that it may enable liquid and/or humidity to be transported there through.

In a further embodiment, the at least one liquid permeable electrode may be formed of a liquid permeable electrically conducting material.

In one embodiment, the liquid permeability may be provided by the electrode being formed of a material that enables liquid and/or humidity to be transported through the material. Such material may be a porous material with a structure enabling such particle transportation. One example of such material may be silver ink. Other examples may be conducting polymers or graphene.

In another embodiment, the at least one liquid permeable electrode may be perforated.

In order to provide liquid permeability through the electrode, the electrode may be perforated. Through holes may be provided through which liquid and/or humidity may be transported. In one embodiment, such holes may be about 0.5-1 mm in diameter, and may be arranged with a distance to each other of about 0.5 cm. The electrode may thereby be formed of a material with suitable conducting properties, without a porous structure enabling liquid and/or humidity transportation. The perforation may enable liquid and/or humidity to reach the substrate such that the substrate may absorb liquid/humidity from the surroundings. The perforation may further enable liquid and/or humidity absorbed by the substrate to be desorbed.

According to a second aspect of the invention, a sensor device for detection of liquid and/or humidity is provided. The sensor device comprises a resonance circuit comprising an inductor connected to a capacitor. The capacitor comprises a first electrode and a second electrode together sandwiching at least a portion of a dielectric substrate. The dielectric substrate comprises a homogeneous material having a dielectric constant which is variable in response to liquid and/or humidity in its environment.

The sensor device according to this aspect of the present invention provides an alternative solution to the same technical problem as the sensor device presented above. The sensor device may be provided to be read by a measuring unit. The resonance circuit may be configured to respond to an interrogation signal from the measuring unit, providing an inductive coupling with the measuring unit. The response signal may be induced in the resonance circuit by the interrogation signal. The properties of the response signal depend on the characteristics of the resonance circuit. For instance, the properties of the response signal may depend on the capacitance value of the capacitor.

The resonance circuit may be a LC circuit. The resonance frequency of the LC circuit may be provided by the inverse of the square root of (VC). The LC circuit may be tuned to resonate at a frequency of about 4-15 MHz, preferably of about 7-9.5 MHz, and most preferably of about 7.1-9.1 MHz.

By homogeneous it may be meant a material devoid of pockets of liquid or gas. The dielectric constant of the substrate may affect the capacitance value of the capacitor. The substrate material may be configured to absorb liquid and/or humidity in its environment. Such liquid/humidity may provide water or moisture of the humidity of the environment of the sensor device. Hence, the capacitance value of the capacitor may vary depending on the surrounding humidity of the sensor device. The amount of liquid and/or humidity that may be absorbed by the substrate may be linear to the presence of liquid and/or humidity. When absorbing the liquid and/or humidity, the substrate's dielectric constant may change. More absorbed particles may provide an increased dielectric constant. An increased dielectric constant may provide an increased capacitance value of the capacitor, and thereby a decreased resonance frequency of the circuit. By using a substrate that has a dielectric constant which may vary in response to the presence of liquid and/or humidity, the capacitance value of the capacitor may vary. It may thereby be possible to detect the presence of liquid and/or humidity of the surrounding by means of the substrate's dielectric constant. This may especially be important when the content of liquid around the sensor device is in such extent that there is no free liquid in the environment, but humidity of the surroundings.

In one embodiment, the dielectric substrate material may be configured to absorb liquid and/or humidity, and the material retains its dimensions +/−0.1%, preferably +/−0.01%, after a complete absorption-desorption cycle.

The dielectric substrate material may be configured to retain its physical dimensions after a complete absorption-desorption cycle. By such cycle it may be meant that the substrate in a first process absorbs liquid and/or humidity in the humidity of the environment at the sensor device up to a value, and in a second process desorbs the corresponding amount of liquid and/or humidity. The dielectric constant of the substrate may thereby be substantially the same prior the absorption-desorption cycle as after. By retaining its physical dimensions, it may be meant a retention of its dimensions +/−0.1%, preferably +/−0.01%. The capacitance value of the capacitor may thereby not be affected by any change in dimensions of the substrate over time. A material with these properties may be suitable for the substrate.

In one embodiment, dielectric substrate may comprise at least 70% by weight of a polymer selected from a group consisting of polyimides and polyethylene-tetrafluorides.

A substrate comprising polyimide or polyethylene-tetrafluoride may provide a suitable liquid and/or humidity absorption capacity without significant dimensional change, while at the same time provide a varying dielectric constant in response to liquid and/or humidity in its environment. Optionally, the substrate may consist essentially of said polymer. Further, optionally, the substrate may consist of said polymer.

The dielectric substrate may in one embodiment have a thickness less than 2 mm, preferably less than 1 mm, or more preferably less than 0.5 mm.

In one embodiment, at least one of the first electrode and the second electrode may be liquid permeable.

In order to detect the presence of liquid and/or humidity in the environment of the sensor device, the liquid and/or humidity may need to get in contact with the substrate. To facilitate such process, at least one of the electrodes may be liquid permeable. By being liquid permeable it may be meant that the electrode is formed such that it may enable liquid and/or humidity to be transported there through.

In a further embodiment, the at least one liquid permeable electrode is formed of a liquid permeable electrically conducting material.

In one embodiment, the liquid permeability may be provided by the electrode being formed of a material that enables liquid and/or humidity to be transported through the material. Such material may be a porous material with a structure enabling such particle transportation. One example of such material may be silver ink. Other examples may be conducting polymers or graphene.

In another embodiment, the at least one liquid permeable electrode may be perforated.

In order to provide liquid permeability through the electrode, the electrode may be perforated. Through holes may be provided through which liquid and/or humidity may be transported. In one embodiment, such holes may be about 0.5-1 mm in diameter, and may be arranged with a distance to each other of about 0.5 cm. The electrode may thereby be formed of a material with suitable conducting properties, without a porous structure enabling liquid particle transportation. The perforation may enable liquid and/or humidity to reach the substrate such that the substrate may absorb liquid/humidity from the surroundings. The perforation may further enable liquid and/or humidity absorbed by the substrate to be desorbed.

In one embodiment, the first and second electrodes may be configured to provide an overlap mismatch relative to each other, wherein the overlap mismatch area is at least 0.1% of the overlapping area of the two electrodes.

When two electrodes in a capacitor is placed with a mismatch, intentionally or unintentionally, parasitic capacitances, or stray capacitances, may occur when the capacitor is powered. The invention is based on the recognition that the resulting capacitance value of the capacitor may increase when a solvent, and in particular a polar solvent, such as water, is present around the sensor device. The dielectric constant of air is in the order of 1, and most solid materials have a dielectric constant in the order of 3-5. Water on the other hand has a dielectric constant in the order of 80. Hence, when water is present around the sensor device, the parasitic capacitances will greatly increase.

This effect may be used by intentionally provide an overlap mismatch area between the first and second electrodes and may be detected by interrogating the sensor device by measuring a resonance response signal of the circuit in the sensor device. The parasitic capacitances may affect the value of the capacitor and thereby affect the resonance frequency of the resonance LC circuit. The resonance frequency of the LC circuit may be provided by the inverse of the square root of (L*C). The LC circuit may be tuned to resonate at a frequency of about 4-15 MHz, preferably of about 7-9.5 MHz, and most preferably of about 7.1-9.1 MHz. The level of parasitic capacitances may make the resonance frequency of the circuit to differ within said interval. The frequency of a response signal provided by the sensor device when receiving an interrogation signal may thereby be used for detecting the presence of a liquid at the sensor device's location.

The overlap area may be of the size of the common area of the substrate along which both the first and the second electrode extends on the respective opposite sides of the substrate. The mismatch area may be the sum of the parts of the first electrode's and the second electrode's respective extension areas minus the overlap area. I.e. the area of the substrate on which either of the electrodes extend without a corresponding other electrode extending to the same area on the opposite side of the substrate. In an exemplary embodiment, one of the electrodes may have a size of 35*18 mm. The other electrode may have a size of 34.5*17.5 mm, such that the larger electrode may extend 0.25 mm outside the extension of the smaller electrode an all four sides thereof. The overlap area may thereby be 603.75 $mm^2$, and the mismatch area may be 26.25 $mm^2$, equal to 4.3% of the overlap area. Both larger and smaller mismatch area relative to the overlap area may be suitable. For instance, the greater electrode may extend outside the overlap area in only one direction by 0.25 mm. The mismatch area may thereby be 0.7% of the overlap area. With a larger overlap area, for instance 65*65 mm, such mismatch extension of 0.25 mm in one direction may provide a mismatch area of 0.4%.

A mismatch area of at least 0.1% of the overlap area may be desired. In one embodiment preferably at least 0.5%. In another embodiment preferably at least 1%. In a further embodiment at least 2%. In a yet further embodiment at least 3%.

Further, the mismatch area may in one embodiment be less than 20% of the overlap area. In another embodiment less than 15%.

By using a first capacitor with electrodes having an overlap mismatch, not only may the dielectric constant of the substrate vary, but also the parasitic capacitances, both of which may contribute to a varying capacitance value of the capacitor. It may thereby not only be possible to detect the presence of liquid or humidity by means of the parasitic capacitance, but also to measure the relative humidity of the surrounding by means of the substrate's dielectric constant. This may especially be important when not only humidity of the surroundings is present, but also free liquid.

In a further embodiment, one of the first and second electrodes may provide a greater electrode area than the other of the electrodes.

In order to intentionally introduce a certain amount of parasitic capacitances, the electrodes may be placed with an intended overlap mismatch. Such mismatch may be provided by one of the electrodes being larger, i.e. having a greater electrode area, than the other one of the electrodes. A desired amount of mismatch may thereby be secured. The larger electrode may be either the first electrode being on the same face side of the substrate as the inductor, or the second electrode arranged on the opposite second face side of the substrate.

In a yet further embodiment, the electrode providing a greater electrode area extends in a plane in parallel to the other of the two electrode, and wherein said electrode with greater electrode area provides a greater extent in at least one direction in said plane than the other of the electrodes.

The electrode that may provide a greater electrode area may provide a greater extension in only one direction along the plane. Alternatively, the larger electrode may provide a greater extension in a plurality of directions in said plane. The extension of the larger electrode may be designed to provide a desired amount of parasitic capacitances.

In one embodiment, the first electrode may be formed on a first face side of the dielectric substrate, and the inductor may be formed as a planar inductor on said first face side of the dielectric substrate.

The sensor device may be formed of the dielectric substrate with the first electrode and the inductor formed on the first face side of the dielectric substrate and the second electrode formed on a second face side of the dielectric substrate, said second face side being opposite said first face side. The inductor may be in electrical connection with the first electrode. The electrodes and the inductor may be printed on the substrate. The first electrode and the inductor may be formed of a common material on the first face side.

In one embodiment, the connection between the inductor and the second electrode of the capacitor may be provided by a connection element.

The connection element may provide a connection between the inductor being formed on the first face side of the substrate and the second electrode being formed on the second face side. The connection element may provide a connection through the substrate.

In a further embodiment, the connection element may comprise a resistive element or a capacitive element.

Said capacitor may be a first capacitor, and the connection element in the form of a capacitive element may be provided as a second capacitor. The second capacitor may be formed of a third electrode and a fourth electrode. The third electrode may be formed on the first face side of the substrate. The fourth electrode may be formed on the second face side of the substrate. The third electrode may be in electrical connection with the inductor. The fourth electrode may be in electrical connection with the second electrode of the first capacitor. The second capacitor may preferably be arranged with an overlap mismatch in the same way as the first capacitor. Hence, the overlap mismatch area between the third and fourth electrodes of the second capacitor may be at least 0.1% of the overlap area, in one embodiment preferably at least 0.5% and in another embodiment preferably at least 1%. In a further embodiment the mismatch area may be at least 2% of the overlap area. In a yet further embodiment at least 3%. Further, the mismatch area may in one embodiment be less than 20% of the overlap area. In one exemplary embodiment, one of the electrodes in the second capacitor may have an area of 60*10 mm, and the other of the electrodes may have an area of 59.5*9.5 mm, such that the larger electrodes extends by 0.25 mm outside the smaller electrode's extension on all four sides thereof. The overlap area may thereby be 565.25 mm$^2$, and the mismatch area 34.75 mm$^2$, providing the mismatch area to be 5.8% of the overlap area.

By providing a second capacitor, the electrical connection between inductor and the first capacitor may be provided in suitable arrangement on the respective face sides of the substrate. A first end of the inductor may be connected to the first electrode of the first capacitor, and the second capacitor may provide a connection from a second end of the inductor arranged on the first face side of the substrate to the second opposite face side of the substrate and further to the second electrode of the first capacitor.

The connection element may further be provided as a resistive element extending through the substrate from a first face side of the substrate to a second opposite face side of the substrate. The resistive element may be connected to the inductor on the first face side and to the second electrode on the second face side.

The resistive element may be formed of a first connector member on the first face side of the substrate, and a second connector member on the second face side of the substrate, wherein one of the connector members extends through the substrate to be in direct connection with the other one of the two connector members. The connection element may be formed as a resistive element extending through the substrate. The two connector members may be formed of separate materials. In a preferred embodiment, the second connector member may be arranged to extend through the substrate. In one embodiment, the connection element may be formed by first arranging the first connector member on the first face side of the substrate. Next a hole through the substrate may be provided at the location of the first connector member, but which hole may not extend through the first connector member. Such hole may be provided by means of e.g. laser etching. Next, the second connector member may be formed by arranging a material therefore on the second face side of the substrate, wherein said material may further fill the hole.

Alternatively, the resistive element may be provided as an element formed of a single material extending from the first face side to the second face side through said hole in the substrate.

When using a resistive element as the connection element, the size of the first capacitor may be reduced since a more effective electrical connection between the components of the resonance circuit may be provided.

In one embodiment, the first electrode may comprise a metal layer.

The first electrode may be provided on the substrate as a metal layer. The metal layer may be a patterned metal film. All components on the first face side of the substrate may be formed of the same material, i.e. the first electrode and the inductor. In an embodiment wherein a second capacitor is provided, also the third electrode of the second capacitor arranged on the first face side may be formed of said material. In an embodiment wherein a connection element is provided, also a portion of the resistive element, such as a connector member, of the connection element arranged on the first face side of the substrate may be formed of the same material. Alternatively, the first electrode and the inductor may be formed of different conducting materials. Similarly, the first electrode and/or the inductor may be formed of a different conducting material than the third electrode or resistive element portion.

The metal layer may in one embodiment comprise Aluminum or Copper. Other conducting materials may alternatively be used.

The first electrode, as well as optionally other components on the first face side of the substrate, may be formed by printing of an electrically conductive ink or polymer.

In a further embodiment, the second electrode may comprise an electrically conductive ink or polymer.

The electrically conductive ink or polymer may for instance be a silver containing ink, a conducting polymer or graphene. The electrically conductive ink or polymer may have been printed on the substrate, for instance by screen printing. A second electrode formed of an electrically conductive ink or polymer may provide an electrode being liquid permeable in order to enable liquid and/or humidity to reach the substrate between the electrodes. All components on a first face side of the substrate may be formed of the same material. In an embodiment wherein a second capacitor is provided, also the fourth electrode of the second capacitor arranged on the second face side of the substrate may be formed of the electrically conductive ink or polymer. In an embodiment wherein a connection element is provided, also a connector member of the connection element arranged on the second face side of the substrate may be formed of the electrically conductive ink or polymer. Further, the connector member of the connection element extending through the substrate may be formed of the electrically conductive ink or polymer.

According to a third aspect of the invention, a system for detecting presence of liquid and/or humidity is provided, the system comprising a sensor device according to any of the embodiments above, wherein the sensor device is arranged at a depth of 0.1-500 mm from an exposed surface of a structure to be analyzed, and a measuring unit comprising an inductive member and a controller. The controller is configured to provide an interrogation signal to the inductive member and to receive a response signal from the inductive member.

The system may be provided to enable a wireless reading of the sensor device, and thereby a measuring of a liquid and/or humidity level detected by the sensor device. As discussed above, the sensor device may comprise a passive circuit configured to backscatter a response signal when receiving an interrogation signal, wherein the resonance frequency of the circuit varies in response to the presence of liquid and/or humidity in its environment. The measuring unit may be configured to send an interrogation signal towards the sensor device. An inductive coupling may thereby be provided between the measuring unit and the sensor device. The inductive member in the measuring unit may function as an antenna, and the controller may provide the intended interrogation signal. The interrogation signal may be sent wirelessly towards the sensor device which may be arranged at a depth below or behind an exposed surface of a structure to be analyzed. The sensor device may be arranged on a part of the structure or may be enclosed inside a material of the structure. The measuring unit may further be configured to receive a response signal from the sensor device and to determine the presence of liquid and/or humidity based on the properties of the response signal.

The structure to be analyzed may be a building part, such as a wall, a floor, a ceiling or a roof.

According to a fourth aspect of the invention, a method for detecting presence of liquid and/or humidity in a structure is provided, the method comprising the steps of providing a sensor device for detection of liquid and/or humidity at a depth of 0.1-500 mm from an exposed surface of the structure, providing an interrogation signal to the sensor device by means of a controller and an inductive member in a measuring unit, receiving a response signal from the sensor device, and detecting the presence of liquid and/or humidity based on the response signal.

The method of detecting presence of liquid and/or humidity may be performed by a system as described above. The provided sensor device may be configured to backscatter a response signal when provided with an interrogation signal from a measuring unit. The interrogation signal may be sent by the inductive member functioning as an antenna, and be directed towards the sensor device. The circuit of the sensor device may be configured to respond with a response signal sent by its inductor in its resonance frequency. The received response signal may then be used for determining the detected presence of liquid and/or humidity. Due to the arrangement of the sensor device, the resonance frequency may vary depending on the presence of liquid and/or humidity. The frequency of the received response signal may thereby vary in response to the presence of liquid and/or humidity. The detection of the presence of liquid and/or humidity may thereby be based on the frequency of the received response signal.

In one embodiment, the sensor device may be a sensor device as described in any of the embodiments above.

In one embodiment, detecting the presence of liquid and/or humidity may comprise associating the response signal with a detected liquid and/or humidity level.

The received response signal(s), received by the measuring unit, may be used to detect the presence of liquid and/or humidity at the location of the sensor device. The properties of the response signal may be used for associating the received response signal to a certain level of detected liquid and/or humidity.

In a further embodiment, detecting the presence of liquid and/or humidity may comprise determining the frequency of the response signal to associate said frequency with a detected liquid and/or humidity level.

The resonance frequency of the sensor device circuit may vary in response to the presence of liquid and/or humidity in the environment of the sensor device. The frequency of the received response signal backscattered from the sensor device may thereby indicate a level of liquid and/or humidity at the sensor device. The detection of liquid and/or humidity may thereby comprise a step of determining the frequency of the response signal and associate said frequency with a detected liquid and/or humidity level. The association may be made by means of a lookup table in which a certain signal frequency response is specified to correspond to predetermined liquid or humidity level.

In one embodiment, providing an interrogation signal may comprise providing at least two interrogation signals at different frequencies, and the step of receiving a response signal may comprise receiving at least two response signals at corresponding frequencies.

The resonance frequency of the circuit in the sensor device may vary depending on the presence of liquid and/or humidity. By providing at least two interrogation signals at different frequencies, the accuracy of the detection of the presence of liquid and/or humidity based on the received response signals may increase.

In a further embodiment, providing an interrogation signal may comprise providing a plurality of interrogation signals at successively decreasing or increasing frequencies within a first frequency range and receiving the response signal may comprise receiving corresponding plurality of response signals.

The range in which the resonance frequency of the sensor device circuit may vary based on the presence of liquid and/or humidity may be known as a first frequency range. The provided interrogation signal may thereby be provided as an interrogation signal frequency sweep within said first frequency range. A corresponding sweep of response signals in the frequency range will thereby be received by the measuring unit. The accuracy of the determination of presence of liquid and/or humidity may thereby be increased.

In a further embodiment, receiving a plurality of response signals may comprise tuning the resonance frequency of the inductive member of the measuring unit to the corresponding successively decreasing or increasing frequencies as the plurality of interrogation signals.

By providing the resonance frequency of the measuring unit antenna, or inductive member, to follow the frequency sweep of the interrogation signal, the accuracy of the detection may be further improved. It may further improve and optimize the maximum frequency read range of the measuring unit. When the resonance frequency of the sensor device circuit is found by the frequency sweep, the interrogation signal frequency and the resonance frequency of both the sensor device circuit and the inductive member of the measuring unit may all be the same, which may provide an increased sensitivity and accuracy in the detection.

In one embodiment, providing the plurality of interrogation signals at successively decreasing or increasing frequencies within a first frequency range may comprise providing said plurality of interrogation signals at a first step rate within the first frequency range, and further providing, based on the received plurality of corresponding response signals, a plurality of interrogation signals within a sub-range within said first frequency range at a second step rate being higher than the first step rate. The interrogation signals may first be provided within the entire first frequency range. These interrogation signals may be sent in successively decreasing or increasing frequencies, in relatively large steps, providing the first step rate. Further interrogation signals may then be provided within a sub-range of the first frequency range, at successively decreasing or increasing frequencies, in relatively small steps, i.e. in the second step rate being higher than the first step rate. The selection of the sub-range may be based on properties of the received plurality of response signals. For instance, the frequency of the response signal determined to be closest to the present resonance frequency of the sensor device may be used as basis for setting the sub-range. A fine tuning of the frequency sweep may thereby be provided in a range closest to the present resonance frequency. An increased accuracy of the detection of liquid and/or humidity may thereby be provided.

In another embodiment, determining the frequency of the response signal may comprise comparing the response signal power level of a plurality of received response signals at different frequencies in said first frequency range, wherein the frequency of the response signal with the maximum signal power level may be used for detecting the presence of liquid and/or humidity.

When providing interrogation signals in a frequency sweep, the signal power levels of the corresponding received response signals at the plurality of frequencies in the first frequency range may be compared in order to find the response signal with maximum signal power level. The maximum leveled response signal may be provided at the resonance frequency of the sensor device circuit. Hence, when the maximum leveled response signal is found, that signal may provide information of the present resonance frequency of the sensor device circuit. That resonance frequency may be used for associating the response signal with a detected liquid and/or humidity level.

In another embodiment, the plurality of interrogation signals may be sent with a common phase, and the phases of the plurality of received response signals are determined and used for detecting the presence of liquid and/or humidity. The interrogation signals sent at successively decreasing or increasing frequencies may be controlled to have the same phase. The phases of the received response signals may differ based on the properties of the sensor device. The phase of the response signal for an interrogation signal at the present resonance frequency of the sensor device may differ from the phase of a response signal for an interrogation signal below or above the resonance frequency. By determining the phases of the plurality of response signals, the resonance frequency may thereby be identified and used for the detection of liquid and/or humidity.

In a further embodiment, a response signal out of the plurality of received response signals, which is in phase with the sent interrogation signals, may be used for detecting the presence of liquid and/or humidity. Alternatively, the response signal out of the plurality of received response signals, which has a phase closest to the phase of the interrogation signals, may be used for detecting the presence of liquid and/or humidity. An interrogation signal sent at the present resonance frequency of the sensor device may provide a received response signal being in phase with the sent interrogation signal. An interrogation signal at a frequency below or above the present resonance frequency of the sensor device may provide a response signal being out of phase with the interrogation signal. An interrogation signal below the resonance frequency may provide a response signal phase being before the phase of the interrogation signal, and an interrogation signal above the resonance frequency may provide a response signal being after the phase of the interrogation signal. A detection of the liquid and/or humidity using the phase of the response signal may provide an exact and efficient detection process, thereby resulting in a reliable detected liquid and/or humidity value.

In one embodiment, said interrogation signal may be a first interrogation signal, and the method may further comprise a step of providing a second interrogation signal comprising providing a plurality of interrogation signals at successively decreasing or increasing frequencies within a second frequency range, and the step of receiving a response signal may comprise receiving corresponding plurality of response signals.

The providing of interrogation signal sweep may be provided in two separate sweeps in two frequency ranges. Different properties of the response signal frequencies may thereby be determined. In an embodiment wherein the sensor device comprises both the first capacitor with an overlap mismatch of the electrodes, and a substrate of a material with dielectric constant varying in response to an absorbed amount of liquid and/or humidity, the two sweeps in the two frequency ranges may be provided to read the two parts respectively. The interrogation signal sweep in the first frequency range may be made mainly to detect the presence of humidity provided by the amount of absorbed humidity by the substrate. The second interrogation signal sweep may be made mainly to detect the presence of liquid provided by the amount of parasitic capacitances from the first capacitor. The substrate may absorb the humidity up to a level wherein no further particles may be absorbed, corresponding to a humidity level of about 100%. Thereafter, free liquid may be present, which may not further affect the dielectric constant of the substrate. The amount of free liquid may then be detected, in response to which the parasitic capacitances may vary, and thereby the resonance frequency of the circuit.

In a further embodiment, the second frequency range may be at least partially outside the first frequency range.

The first and the second frequency range may comprise separate frequencies, but may overlap. The overlap range may be less than half of each of the frequency ranges.

In one embodiment, the first frequency range may be on the order of 7.5-9.1 MHz. Further, the second frequency range may in one embodiment be on the order of 7.1-7.7 MHz.

In one embodiment, the step of providing a second interrogation signal may be provided only in case the response signal received from the first interrogation signal is assigned to a humidity level greater than 95% humidity, preferably greater than 100% humidity.

The resonance frequency of the sensor device circuit may vary in response to the presence of liquid and/or humidity in the sensor device's environment. The range in which the resonance frequency may vary may depend on whether liquid is present as humidity or as free liquid. The resonance frequency may first vary in the first frequency range corresponding to the level of humidity up to a level of 100% humidity. Thereafter, the resonance frequency may vary in a range corresponding to the level of present free liquid. In case the humidity level has not reached 100% or at least 95%, a detection of free liquid may not be necessary. A first interrogation signal sweep may thereby be provided in the first frequency range, wherein the first frequency range corresponds, at least partly, to the range in which the resonance frequency may vary in response to the detected humidity level. If the detected humidity level is at least 95% or at least 100%, the second interrogation signal sweep in the second frequency range may be provided, wherein the second frequency range corresponds, at least partly, to the range in which the resonance frequency may vary in response to the detected free liquid level. In an alternative embodiment, the two interrogation signal sweeps in the first and second frequency ranges may be provided as above, but both sweeps may be provided irrespective of the detected humidity level from the first interrogation signal sweep.

In one embodiment, the step of providing a plurality of interrogation signals in the first frequency range with different frequencies may comprise providing at least 100, preferably at least 1000 and most preferably at least 2000, interrogation signals with different frequencies within the first frequency range. Further, the step of providing a plurality of interrogation signals in the second frequency range with different frequencies may in one embodiment comprise providing at least 100, preferably at least 1000 and most preferably at least 2000, interrogation signals with different frequencies within the second frequency range.

Hence, each interrogation signal sweep in the first frequency range and the second frequency range may be provided as at least 100, 1000 or 2000 interrogation signals at different frequencies within the respective frequency range. The resolution of the interrogation signal sweeps may be selected depending on the accuracy needed for the detection of liquid and/or humidity, or depending on the characteristics of the sensor device circuit and its provided response signal.

In another embodiment, the step of providing the interrogation signal may comprise providing the interrogation signal at a first power level, and a step of determining whether the corresponding received response signal is within a predetermined power level range.

The inductive coupling provided between the measuring unit and the sensor device by means of the interrogation signal and the corresponding response signal may change dependent on the distance between the measuring unit and the sensor device. This inductive coupling may further be affected of the power level of the interrogation signal. If the inductive coupling becomes too strong, the resonance frequency of the sensor device circuit may be shifted causing an error in the measurement of the response signal frequency. This may be due to too large currents being induced in the sensor device circuit. A too strong interrogation signal power level may provide a corresponding too strong response signal power level. The power level of the response signal may thereby be used to determine whether a too strong inductive coupling is present. The power level of the received response signal may be compared to a predetermined power level range of the response signal. If the response signal is within said predetermined range, the frequency of the response signal may be reliable and used for the detection of liquid and/or humidity.

In a further embodiment, the step of providing the interrogation signal may comprise, if the received response signal from the first power level interrogation signal is not in the predetermined power level range, providing the interrogation signal at a second power level, and determining whether the corresponding received response signal is within a predetermined power level range.

In a further embodiment, the step of providing the interrogation signal may comprise repeating the steps of the method at successively lower or higher interrogation signal power levels until a corresponding response signal is received which is within the predetermined response signal power level range.

One way to overcome a too strong inductive coupling may be to provide a greater distance between the measuring unit and the sensor device, i.e. to move the measuring unit further away from the sensor device. However, the distance range in which a suitable inductive coupling level is achieved may be narrow and it may be difficult for a user to adjust the distance accurately. Instead, the power level of the provided interrogation signal may be adjusted to one or several additional power levels. By providing a stepwise adjustment of the interrogation signal power level, each corresponding response signal may be compared to the predetermined power level range. When a response signal within the predetermined range is achieved, the interrogation signal power level adjustment may be terminated. Besides providing an improved accuracy and reliability to the detection, the power level adjustment provides an increased flexibility in possible placements of the sensor device. An increased depth of the sensor device placement relative to the exposed surface of the structure may be possible since an increased initial interrogation signal may be used, without the risk that the power level is too high when measuring a sensor device placed at a lower depth.

In one embodiment, the method may comprise determining a first liquid and/or humidity level at a first point in time, and determining a second liquid and/or humidity level at a second point in time, wherein the first and second points in time may be more than one day apart, more than one week apart or more than one month apart, and comparing the first and second liquid and/or humidity levels to determine whether the liquid and/or humidity level has decreased.

The detection of presence of liquid and/or humidity in a structure may be used for determining a change in liquid and/or humidity presence over time. When using the present invention for detection of liquid and/or humidity at the location of a sensor device placed under a liquid impermeable cover layer on e.g. a floor or wall, which cover layer was fastened using a glue comprising a solvent (such as water), the absorption of the solvent by the underlying structure may be controlled by measuring the liquid and/or humidity level at a first point of time close to the application of the glue and cover layer, and at a second point of time being at least one day later, and comparing the results of the two measurements. Preferably, additional measurements may be made at points of time yet later from the application time. A desired absorption process may thereby be controlled.

According to fifth aspect of the invention, a measuring unit comprising a controller and at least one inductive member is provided, wherein the controller and the inductive member are configured to perform the steps of providing an interrogation signal to a sensor device and receive a response signal from the sensor device according to any of the embodiments of the method discussed above.

According to a sixth aspect of the invention, a method for reading a passive wireless sensor device comprising a resonance circuit is provided, wherein the method comprising the steps of providing a wireless interrogation signal to the sensor device by means of an inductive member in a measuring unit, and receiving a response signal from the sensor device. The step of providing the interrogation signal comprises providing a plurality of interrogation signals at successively decreasing or increasing signal power levels until a corresponding response signal is received which is within a predetermined response signal power level range. The method may further comprise a step of comparing the power level of the received signal to a predetermined response signal power level range, and the step of providing the interrogation signals at successively decreasing or increasing signal power levels is performed until a corresponding response signal is received which is determined to be within the predetermined response signal power level range.

The passive wireless sensor device may be a sensor device configured to backscatter a response signal induced by an interrogation signal. The sensor device may comprise a LC circuit having a resonance frequency at which the response signal may be provided. The inductive coupling provided between the measuring unit and the sensor device by means of the interrogation signal and the corresponding response signal may change dependent on the distance between the measuring unit and the sensor device. This inductive coupling may further be affected of the power level of the interrogation signal. If the inductive coupling becomes too strong, the resonance frequency of the sensor device circuit may be shifted causing an error in the receipt of the response signal frequency. This may be due to too large currents being induced in the sensor device circuit. A too strong interrogation signal power level may provide a corresponding too strong response signal power level. The power level of the response signal may thereby be used to determine whether a too strong inductive coupling is present. The power level of the received response signal may be compared to a predetermined power level range of the response signal. If the response signal is within said predetermined range, the frequency of the response signal may be reliable and the reading of the sensor device may be accurate.

One way to overcome a too strong inductive coupling may be to provide a greater distance between the measuring unit and the sensor device, i.e. to move the measuring unit further away from the sensor device. However, the distance range in which a suitable inductive coupling level is achieved may be narrow and it may be difficult for a user to adjust the distance accurately. Instead, the power level of the provided interrogation signal may be adjusted to one or several additional power levels. By providing a stepwise adjustment of the interrogation signal power level, each corresponding response signal may be compared to the predetermined power level range. When a response signal within the predetermined range is achieved, the interrogation signal power level adjustment may be terminated. Besides providing an improved accuracy and reliability to the detection, the power level adjustment provides an increased flexibility in possible placements of the sensor device. An increased distance between the sensor device and the measuring unit may be possible since an increased initial interrogation signal may be used, without the risk that the power level is too high when measuring a sensor device placed at close range.

The sensor device may be a wireless sensor device for detection of liquid and/or humidity. The sensor device may in one embodiment be a sensor device according to any of the embodiments described above.

According to a seventh aspect of the invention, a measuring unit for reading a passive wireless sensor device comprising a resonance circuit, wherein the measuring unit is configured to perform the above method for reading such sensor device.

BRIEF DESCRIPTION OF THE DRAWINGS

The invention will in the following be described in more detail with reference to the enclosed drawings, wherein.

DESCRIPTION OF EMBODIMENTS

Figure 1:
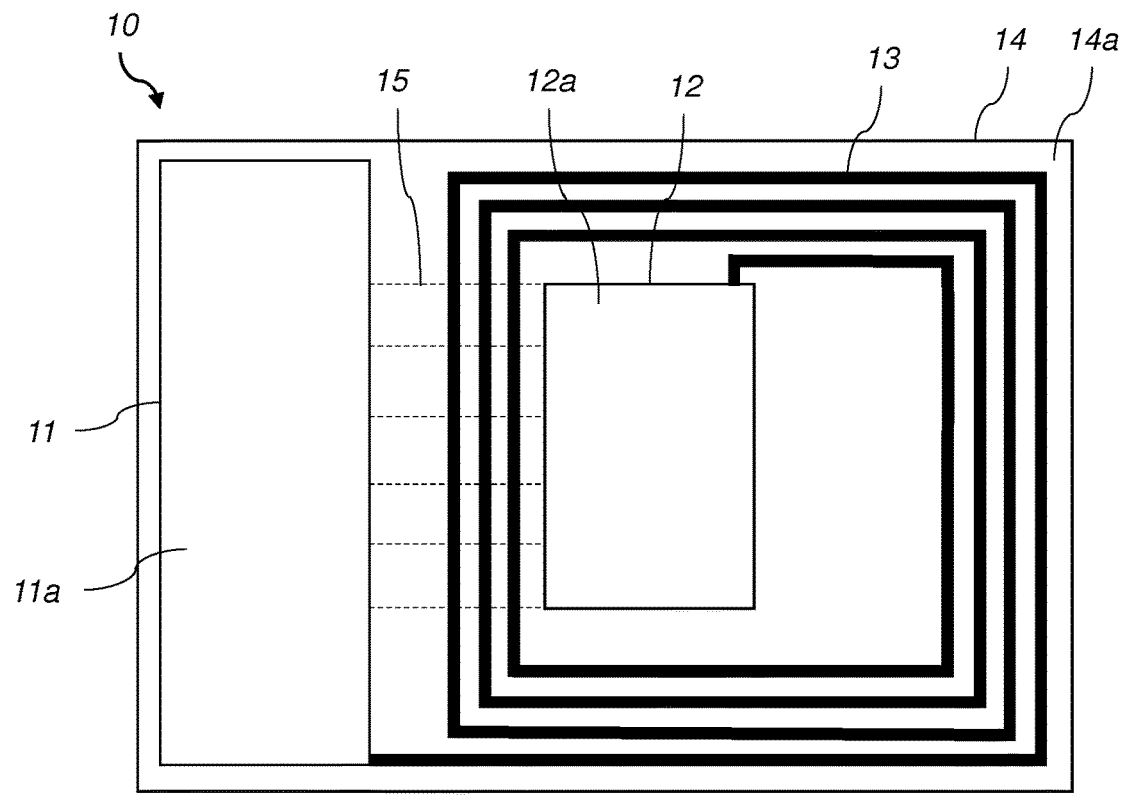
FIG. 1 shows a schematic top view of a sensor device according to an embodiment of the invention.

The present invention will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, like numbers refer to like elements.

FIGS. 1 and 2 illustrate a sensor device 10 comprising a substrate 14 having a first face side 14a and a second face side 14b. On the first face side 14a an inductor 13 is arranged. A first capacitor 11 comprises a first electrode 11a on the first face side 14a and a second electrode 11b on the second face side 14b. The first and second electrodes 11a, 11b sandwiches the substrate 14 to form the capacitor 11. The substrate 14 is a dielectric substrate suitable to form a thin capacitive element by means of electrodes arranged thereon.

The inductor 13 is directly connected to the first electrode 11a on the first face side 14a. The inductor 13 is further coupled to the second electrode 11b, in the illustrated embodiment of FIGS. 1 and 2 via a second capacitor 12 and connection lines 15. The second capacitor 12 comprises a third electrode 12a on the first face side 14a and a fourth electrode 12b on the second face side 14b. The third and fourth electrodes 12a, 12b sandwich the substrate 14 to form the second capacitor 12.

The first electrode 11a, the third electrode 12a and the inductor 13 on the first face side 14a may be formed of a common material, such as Aluminum or Copper or other conducting material. The second electrode 11b, the fourth electrode 12b and the connection lines 15 on the second face side 14b may be formed of a common material, preferably silver ink.

The dielectric substrate 14 may be formed of polyimide, which may be constituted of a homogeneous layer. The polyimide material provides the substrate 14 with the ability to absorb liquid in the humidity of the environment at the location of the sensor device 10. The dielectric constant of the substrate 14 may thus vary in response to the level of absorption by the substrate. The capacitance value of the first capacitor 11 will thereby vary. In the illustrated embodiment wherein the second capacitor 12 is provided, also the capacitance value of the second capacitor 12 will vary. The varying capacitance values of both the first and the second capacitors 11, 12 will affect the resonance frequency of the sensor device 10.

Figure 2A:
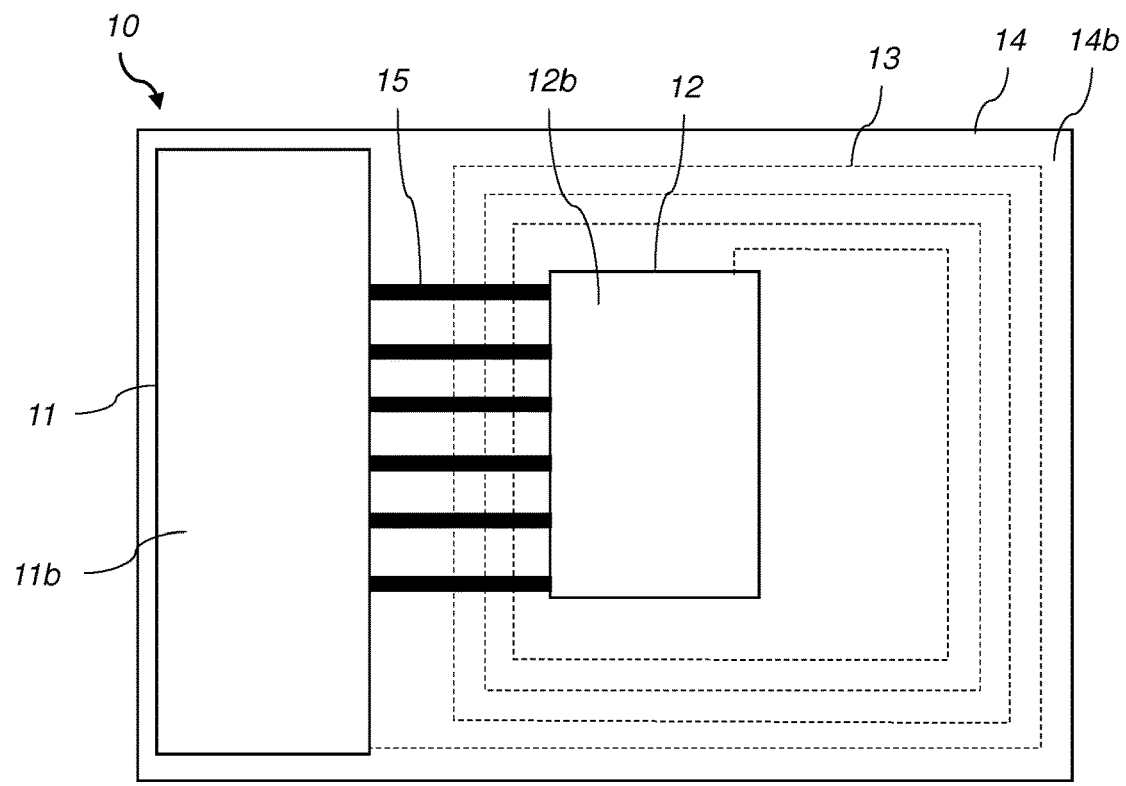
FIGS. 2a-b show schematic bottom views of a sensor device according to embodiments of the invention.
Figure 2B:
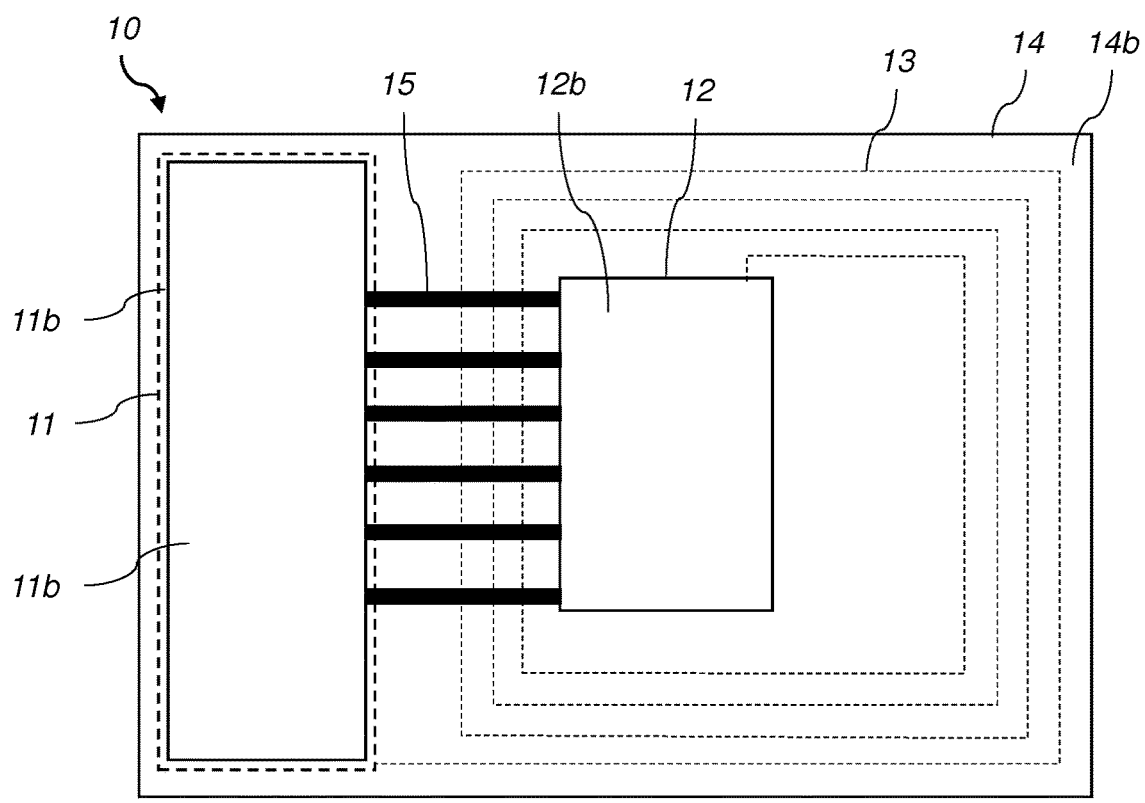
Figure 3:
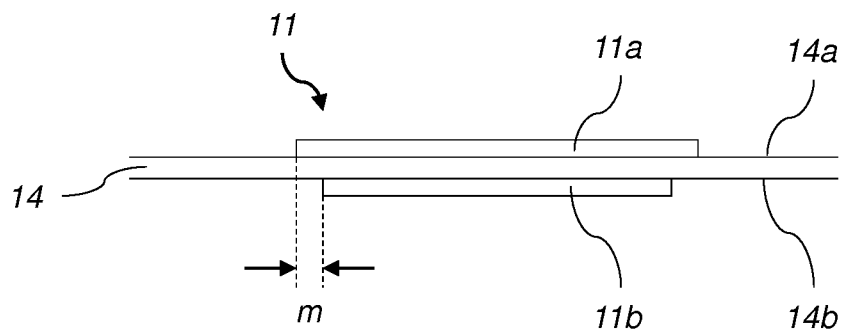
FIG. 3 shows a schematic cross-sectional view of a sensor device according to an embodiment of the invention.
Figure 4A:
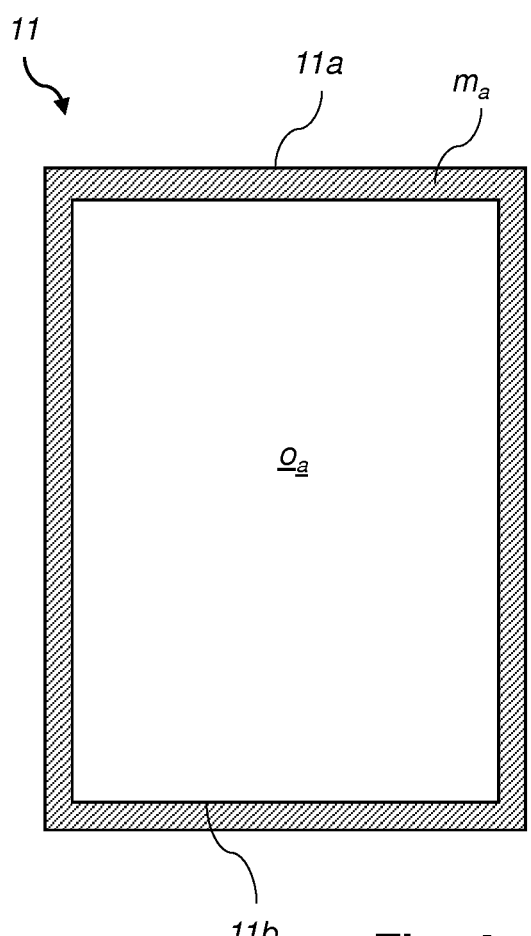
FIGS. 4a and 4b show schematic top views of a capacitor according to embodiments of the invention.

In the embodiment illustrated in FIG. 2a, the first and second electrodes 11a, 11b are of equal size. In the embodiment illustrated in FIG. 2b, the first electrode 11a and the second electrode 11b are formed with an intended overlap mismatch. In FIGS. 1 and 2, and further in FIGS. 3 and 4a, it is illustrated that the first electrode 11a extends over a larger area than the second electrode 11b. As seen in FIG. 3, at least one pair of adjacent outer edges of the first and second electrodes 11a, 11b may be spaced apart by a distance m. In FIG. 4a, the extensions areas of the two electrodes 11a, 11b are visualized such that an overlapping area $o_a$, i.e. the common area to which both the first and second electrodes 11a, 11b abut the substrate 14, is shown.

Further, a mismatch area $m_a$ is shown, being the extension area of the first electrode 11a not having a corresponding extension of the second electrode 11b along the substrate 14. In the embodiment of FIG. 4a, the mismatch area $m_a$ is provided as the extension area of the first electrode 11a minus the extension area of the second electrode 11b. In the illustrated embodiment the first electrode 11a is arranged such that the mismatch area $m_a$ is evenly distributed along the four sides of the electrodes. Alternatively, the mismatch area $m_a$ can be provided along only a part of the circumference of the second electrode 11b. Along the remaining circumference, the edges of the two electrodes 11a, 11b may be in line.

Figure 4B:
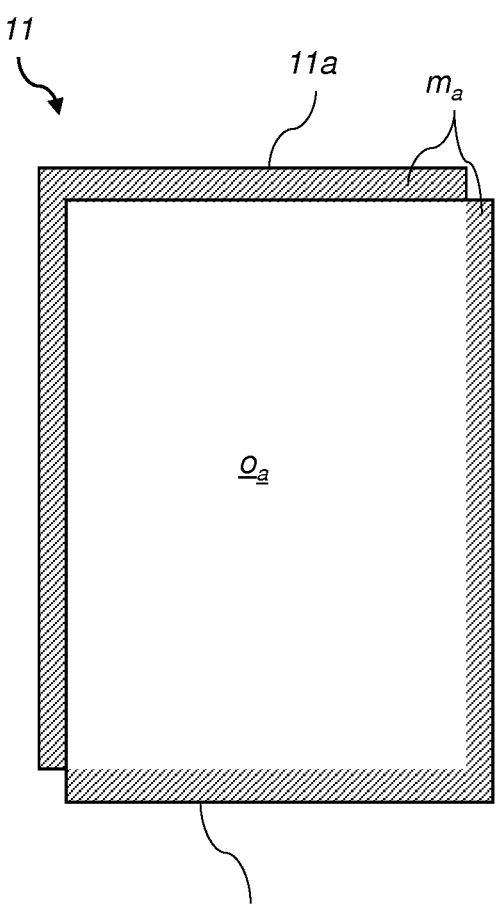

FIG. 4b illustrates an alternative arrangement of the first and second electrodes 11a, 11b. Instead of being of different sizes, the two electrodes 11a, 11b are offset. The overlapping area $o_a$ is correspondingly the common area along the substrate 14 for the two electrodes 11a, 11b. The mismatch area $m_a$ is provided partly by each of the two electrodes 11a, 11b.

The arrangement of the first capacitor 11 having an overlap mismatch $m_a$ provides a generation of parasitic capacitances when a signal is induced in the circuit. The parasitic capacitances are provided intentionally such that they can affect the capacitance value of the first capacitor 11 in response to liquid present in the environment of the sensor device 10.

Figure 5:
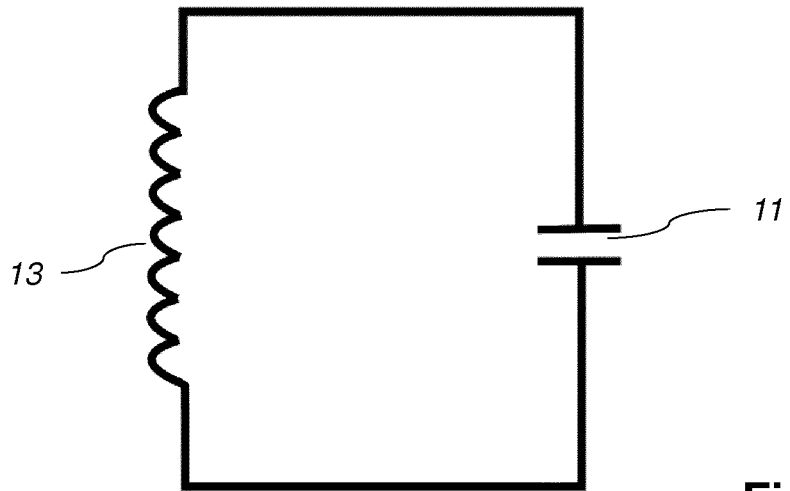
FIG. 5 shows a schematic circuit diagram of a sensor device according to an embodiment of the invention.
Figure 6:
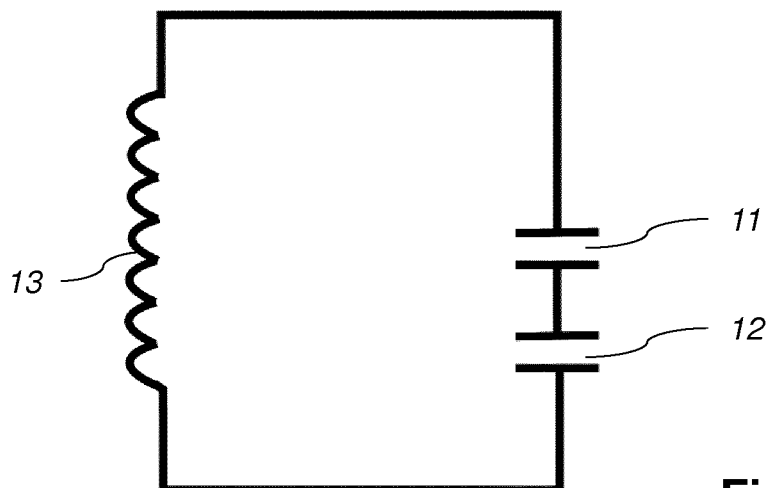
FIG. 6 shows a schematic circuit diagram of a sensor device according to an embodiment of the invention.

FIGS. 5 and 6 illustrate schematic circuit diagrams of the sensor device circuit. The FIG. 5 circuit diagram provide the general circuit used for the function of the sensor device 10 to backscatter a response signal from an interrogation signal, comprising the inductor 13 and the capacitor 11. A direct electrical connection is provided between the inductor 13 and both sides of the first capacitor 11. FIG. 6 illustrates a circuit of the embodiment comprising the second capacitor 12 in series with the first capacitor 11 and the inductor 13.

Figure 7:
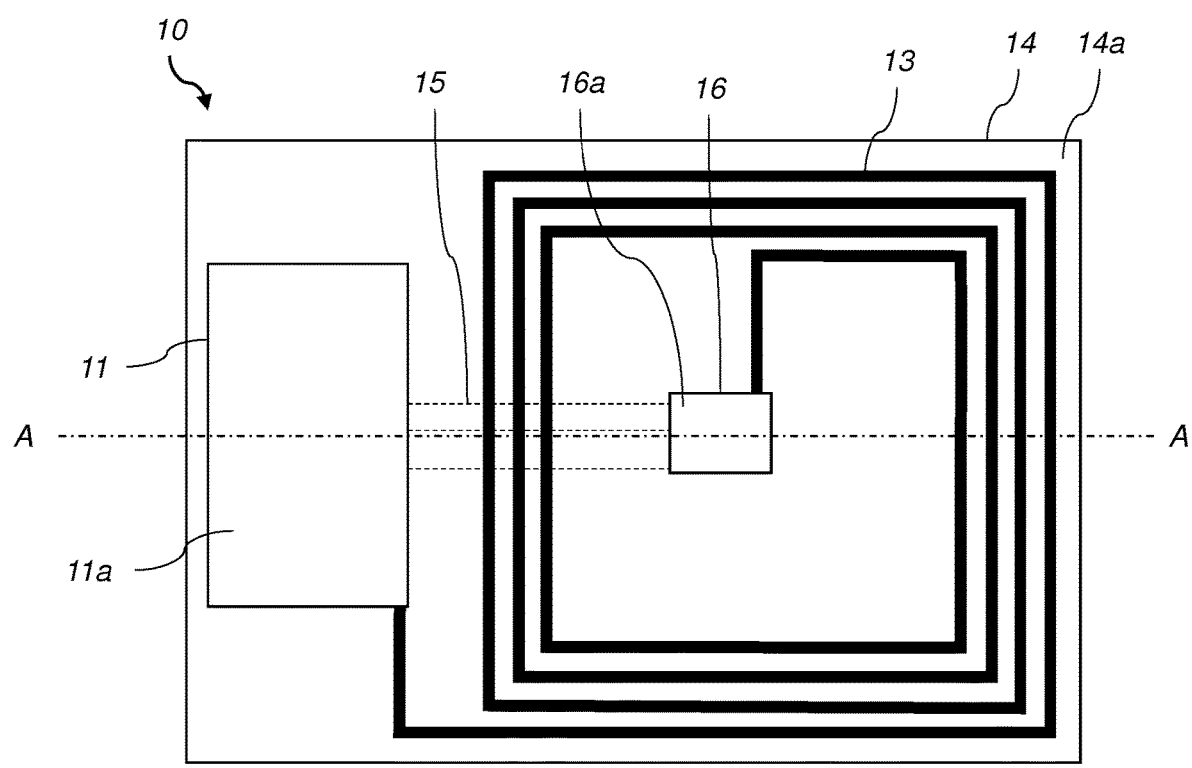
FIG. 7 shows a schematic top view of a sensor device according to an embodiment of the invention.
Figure 8A:
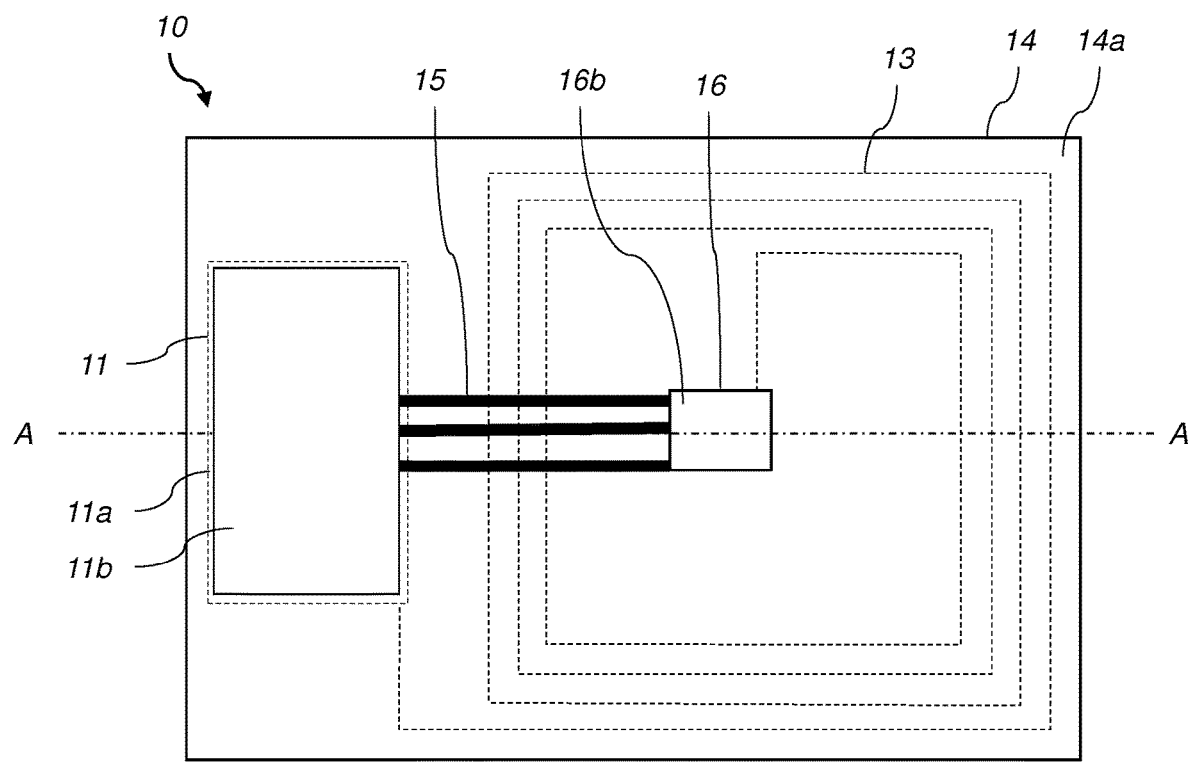
FIGS. 8a-b show schematic bottom views of a sensor device according to an embodiment of the invention.
Figure 8B:
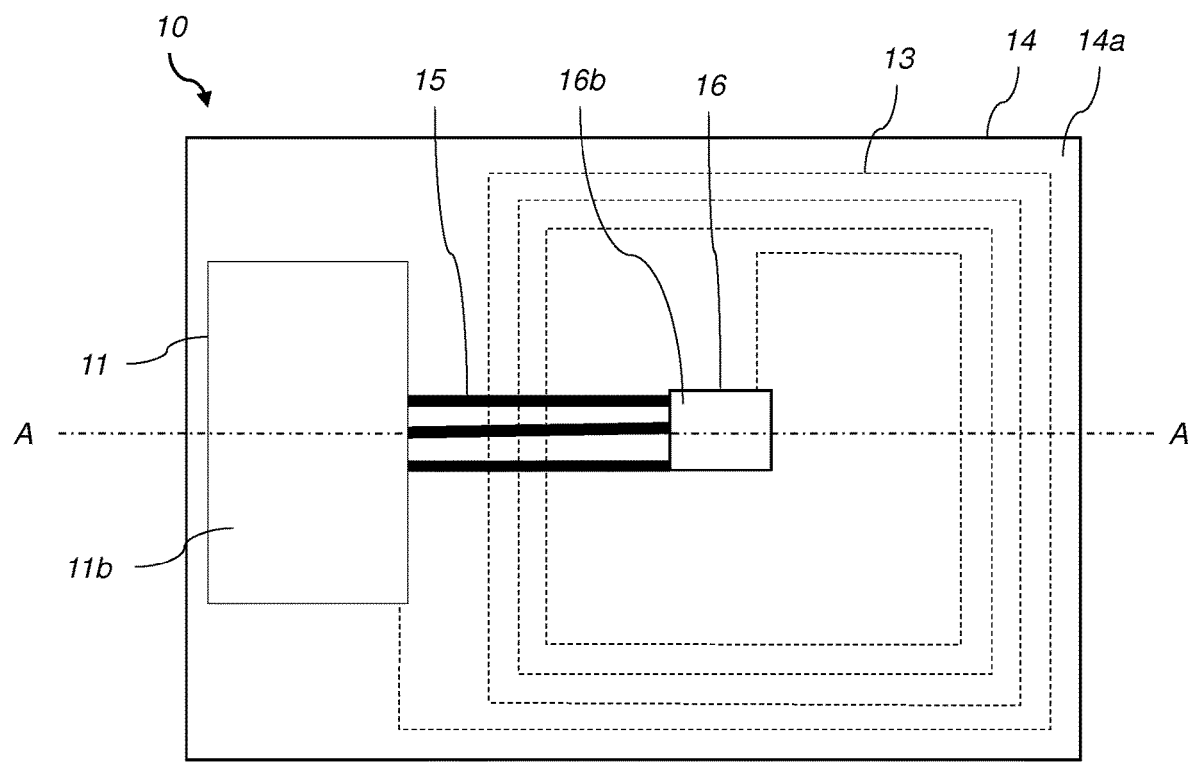

FIGS. 7 and 8a-b illustrate an alternative embodiment of the sensor device 10 wherein the connection between the inductor 13 and the second electrode 11 is provided by a resistive element 16. The resistive element 16 comprises in the illustrated embodiment a first connector member 16a on the first face side 14a and a second connector member 16b on the second face side 14b. On the second face side 14b the second connector member 16b is in connection with the second electrode 11b via the connection lines 15. The first connector member 16a is connected to the inductor 13. In an alternative embodiment, the resistive element 16 may be formed of an element in a single material extending from the first face side 14a to the second face side 14b and further to be in electrical connection with the inductor 13 and the second electrode 11b. As illustrated, the first and second electrodes 11a, 11b may be of equal size or with an intended miss-match area.

Figure 9A:
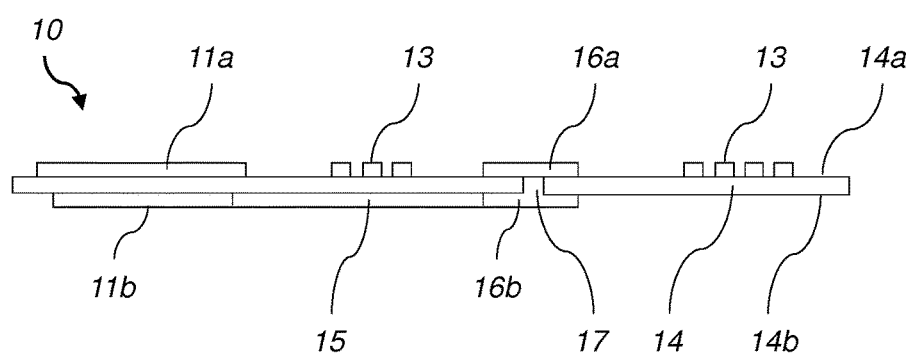
FIGS. 9a-b show schematic cross-sectional views of a sensor device according to embodiments of the invention.
Figure 9B:
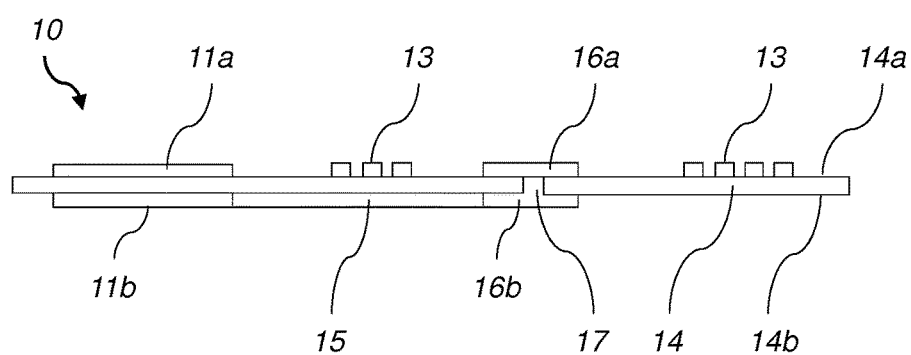

In FIGS. 9a-b the cross-section of the sensor device 10 along line A-A is illustrated. The resistive element 16 is arranged through a hole 17 in the substrate 14 to provide a connection from the first face side 14a to the second face side 14b. One of the first and second connector members 16a, 16b extends through the hole 17 to the other one of the connector members. In the illustrated embodiment, the second connector member 16b extends on the second face side 14b and through the hole 17 to be in connection with the first connector member 16a. A connection between the inductor 13 on the first face side 14a and the second electrode 11b on the second face side 14b is thereby be provided via the resistive element 16 and the connecting lines 15.

Figure 10:
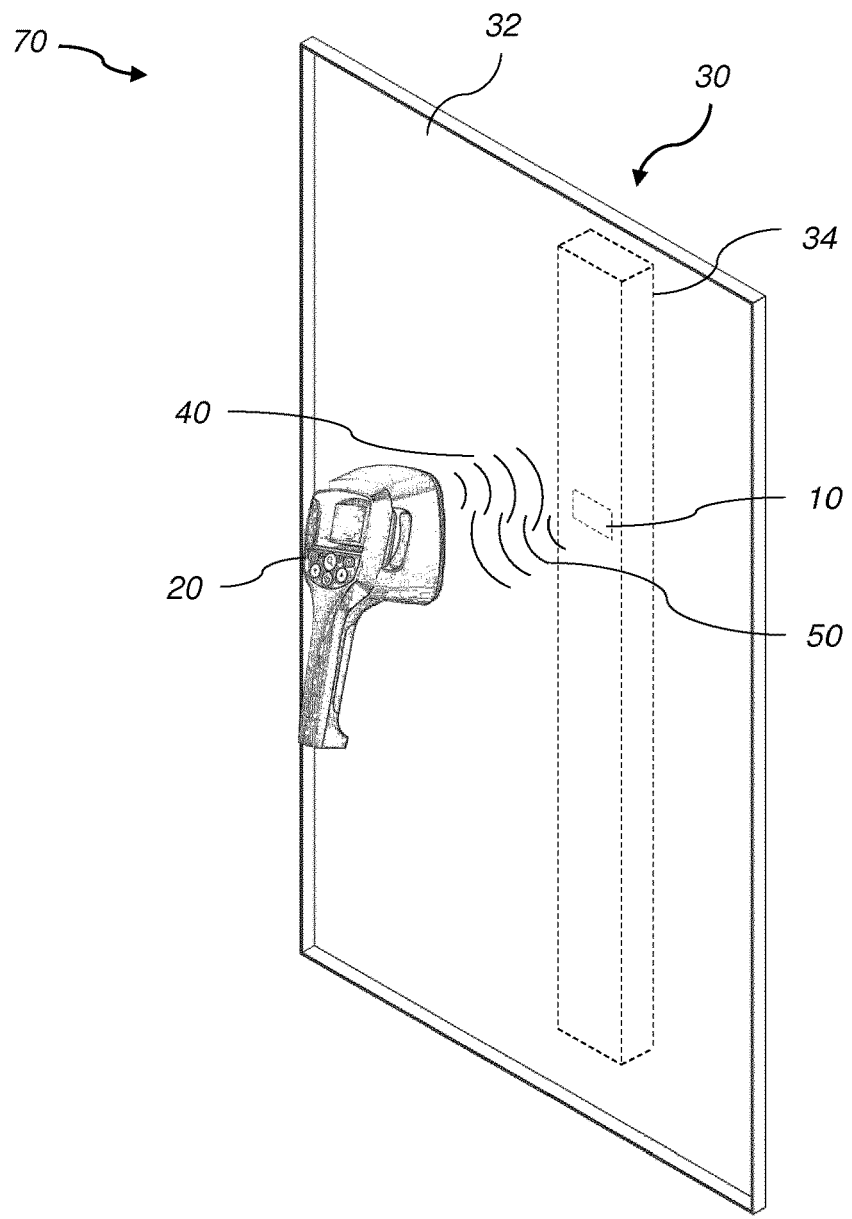
FIG. 10 shows a schematic perspective view of a system according to an embodiment of the invention.
Figure 11:
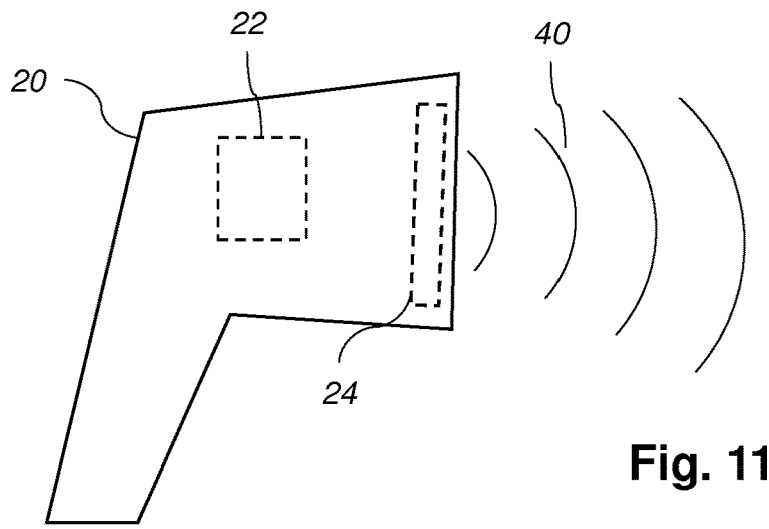
FIG. 11 shows a schematic block view of a measuring unit according to an embodiment of the invention.

FIG. 10 illustrate a system 70 for detecting the presence of liquid and/or humidity in a structure 30. The system 70 comprises a sensor device 10 arranged on a structure part 34 at a distance or depth from an exposed surface 32 of the structure 30. The system 70 further comprises a measuring unit 20 configured to read the sensor device 10. The measuring unit 20 comprises a controller 22 and an inductive member 24 as schematically illustrated in FIG. 11. The measuring unit 20 is configured to send an interrogation signal 40 towards the sensor device 10. The interrogation signal 40 is provided by the controller 22 to the inductive member 24 which provides the wireless transmission thereof. The measuring unit 20 may further comprise a power source, such as a battery, to power the controller, and a user interface to enable a user to control the operation of the measuring unit and to receive information of the detection.

When the sensor device 10 receives the interrogation signal 40, a response signal 50 is induced and returned. The measuring unit 20 receives the response signal 50 by means of the inductive member 24, and the controller uses the response signal 50 to determine a detected liquid and/or humidity level from the sensor device 10.

Figure 12:
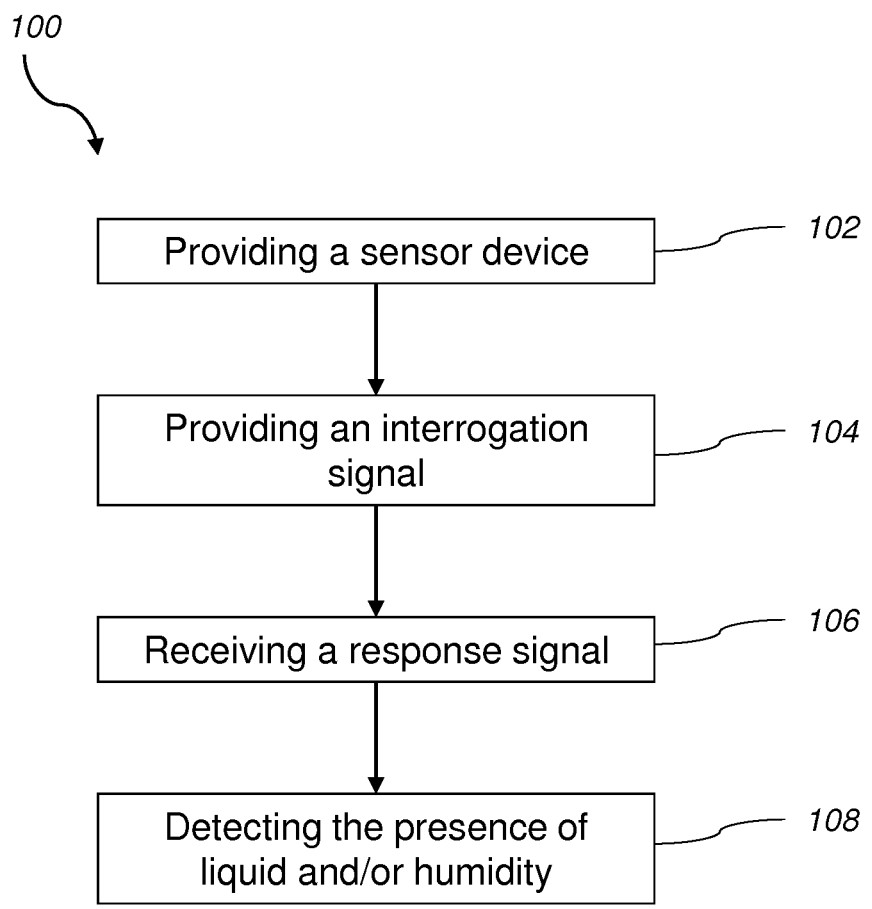
FIG. 12 shows a flowchart of a method according to an embodiment of the invention.

FIG. 12 illustrates a method 100 of detecting the presence of liquid and/or humidity using a system 70 comprising a sensor device 10 and a measuring unit 20. In a first step 102, the sensor device 10 is provided in a structure 30 at the location wherein the presence of liquid and/or humidity is to be detected. The sensor device 10 is configured to react on the presence of liquid and/or humidity by means of the substrate 14 absorbing humidity and thereby affecting the capacitance value of the first capacitor 11, and/or by means of parasitic capacitances affecting the capacitor value of the first capacitor 11 in response to the presence of liquid.

A change of the capacitance value of the first capacitor 10 in response to humidity absorbed by the substrate 14 and/or the parasitic capacitances will change the resonance frequency of the sensor device 10.

In a second step 104, the measuring unit 20 is used for providing an interrogation signal 40 towards the sensor device 10. In a third step 106, a response signal 50 is returned to the measuring unit 20 from the sensor device 10 in response to the interrogation signal 40. The response signal 50 is generated as a backscattered resonance signal induced in the sensor device circuit by the interrogation signal 40. Based on the received response signal 50, the presence of liquid and/or humidity at the location of the sensor device 10 is detected. The response signal 50 is used for detection of a liquid and/or humidity level.

The response signal 50 to be used for the detection 108 is provided at the resonance frequency of the sensor device circuit. The resonance frequency will vary depending on the presence of liquid and/or humidity as described above. A resonance frequency range in which the resonance frequency may vary is known due to properties of the sensor device circuit. The exact resonance frequency at a specific point of time may however not be known since it depends on the presence of liquid and/or humidity at that point of time. In order to receive a response signal 50 in the resonance frequency, the step of providing 104 the interrogation signal 40 comprises in the illustrated embodiment a step of providing a plurality of interrogation signals 40 at successive different frequencies. The frequency sweep interrogation signals are provided in successively decreased or increased frequencies in predetermined steps. The plurality of interrogation signals 40 are provided by the controller 22 to the inductive member 24. The inductive member 24 is correspondingly tuned to receive signals at the same frequencies as the successive interrogation signals.

The received response signals 50 will have different power levels. The maximum response signal power level will be received when the interrogation signal 40 is provided at, or closest to, the resonance frequency of the sensor device 10. The step 106 of receiving the response signal 50 thereby comprises a step of determining the power level of the plurality of received response signals 50 at different frequencies, and the response signal frequency providing the maximum response signal power level is used for the step 108 of detecting the presence of liquid and/or humidity.

Figure 13:
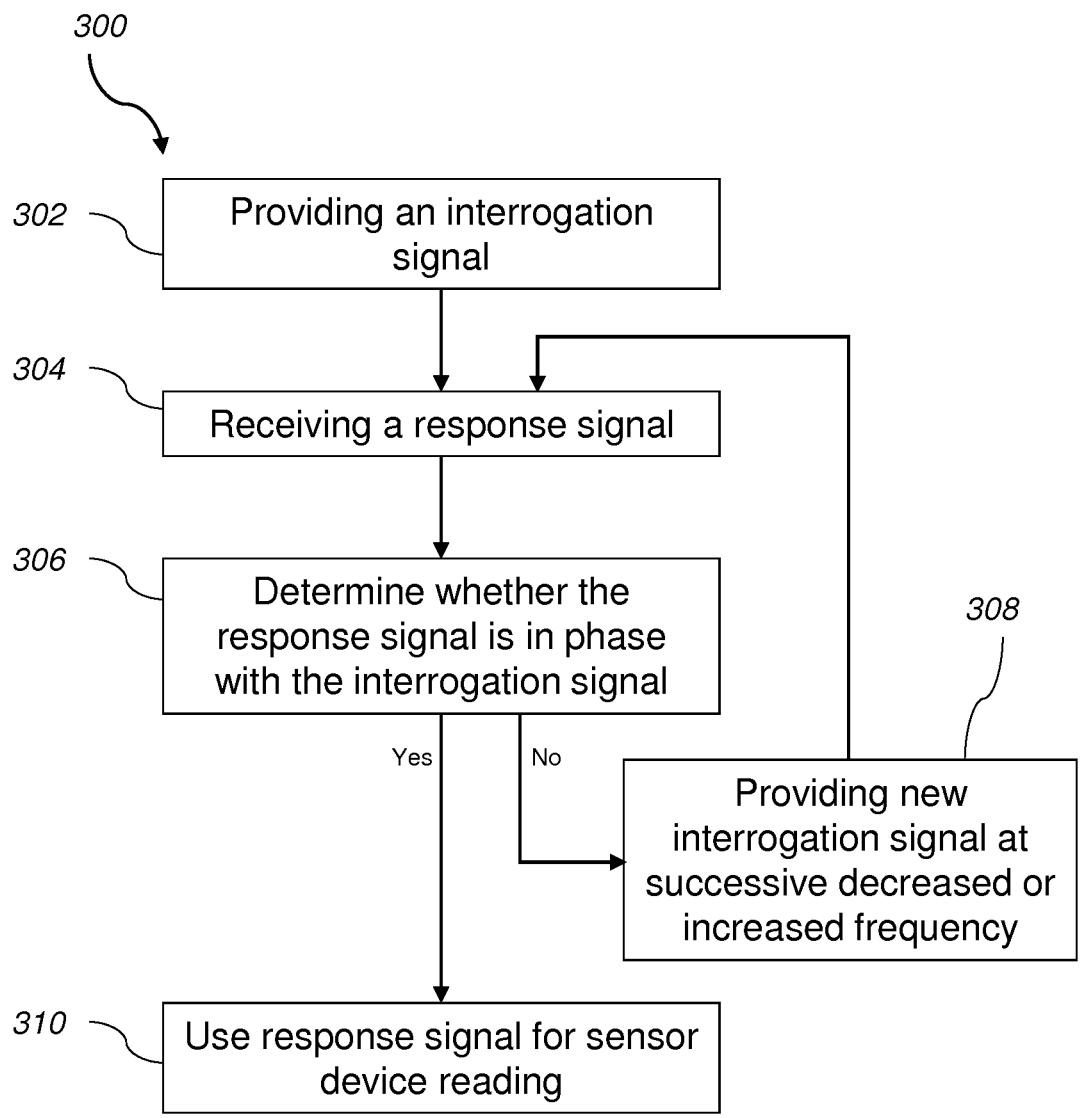
FIG. 13 shows a flowchart of a method according to an embodiment of the invention.

An alternative method 300 to using the power level of the received plurality of response signals 50 is illustrated in FIG. 13. An interrogation signal is sent 302 with a predetermined phase. A response signal is received 304. The phase of the response signal is determined 306. If the response signal is in phase, or within a predetermined range, with the phase of the interrogation signal, the response signal is determined to be received for the present resonance frequency of the sensor device. That received response signal is thereby used 310 for the reading of the sensor device and detection of liquid and/or humidity. If the response signal is not in phase with the interrogation signal, a new interrogation signal is sent 308 at a successive decreased or increased frequency, with the same phase as the previously sent interrogation signal. The phase of the new received response signal is then compared to the phase of the interrogation signal in the same way.

Figure 14:
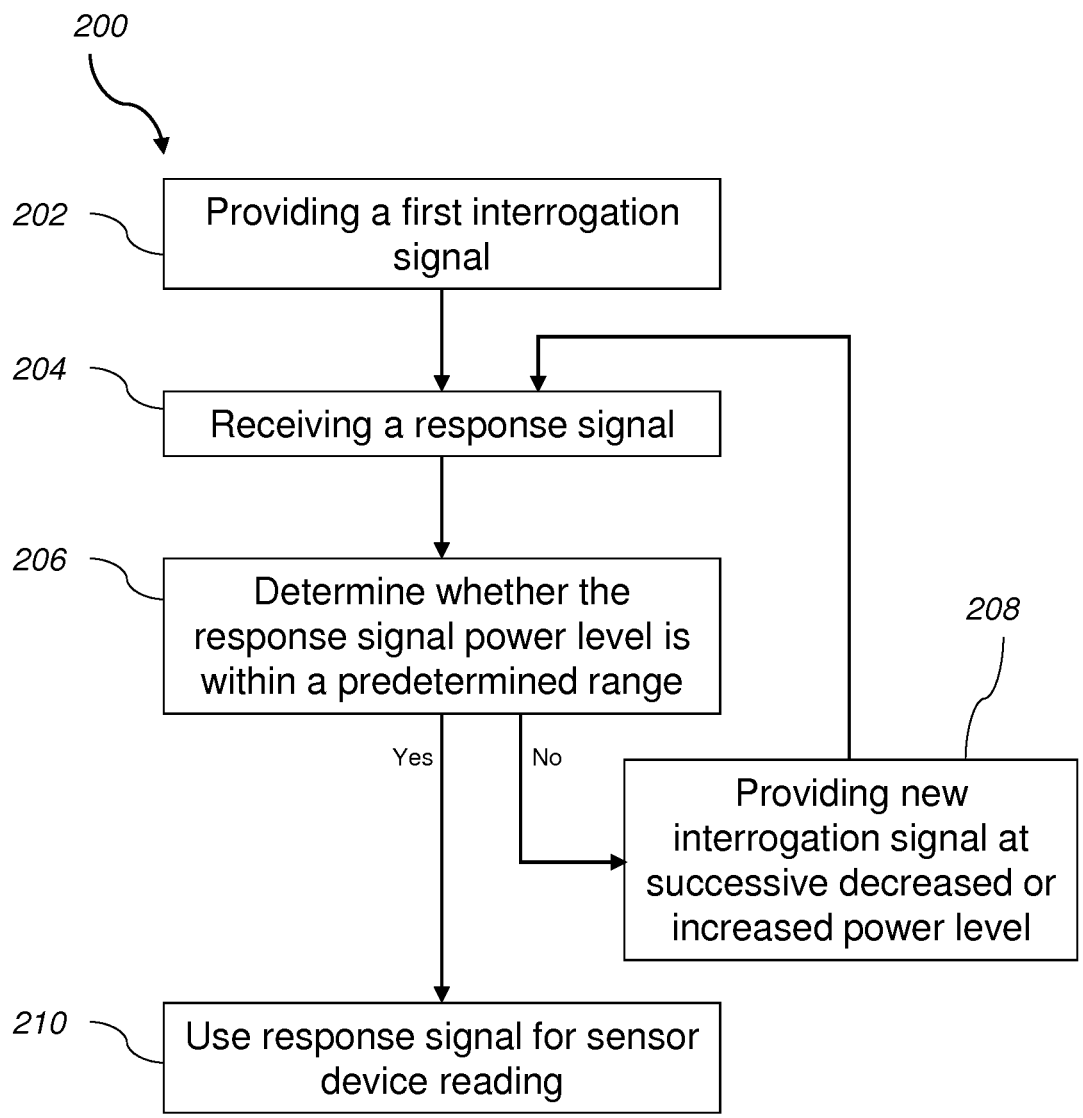
FIG. 14 shows a flowchart of a method according to an embodiment of the invention.

FIG. 14 illustrates a method 200 for reading a passive resonating sensor device 10 wherein an interrogation signal 40 is provided from a measuring unit 20. In the method 200 a first step 202 is provided when providing a first interrogation signal 40 having a first interrogation signal power level. The first interrogation signal is provided to the sensor device 10 and a response signal 50 is returned from the sensor device 10 in the sensor device's resonance frequency and received 204 by the measuring unit 20. The power level of the received response signal 50 is determined 206 by a controller 22 in the measuring unit 20. The response signal power level is compared to a predetermined range. If the received response signal power level is within the predetermined power level range, the response signal 50 is used by the measuring unit 20 for reading the sensor device 10. The response signal power level being in the predetermined range may indicate that the properties of the response signal is reliable.

If the response signal power level is not within the predetermined range, a new interrogation signal is provided 208 by the measuring unit 20 at a successively decreased or increased power level. Steps 204 and 206 may thereby be repeated to determine whether the new received response signal power level is within the predetermined range.

As an alternative, it is possible to always provide a complete set of signals at different power levels, whereby a value may be selected based on some other criterion, such as a power that forms an average of the highest power in-range response and the lowest power in-range response.

The first power level of the interrogation can be at a maximum power level, and the successive interrogation signal power levels, if needed, is decreased power levels in successive steps. The steps may be according to a predetermined step pattern.

In one embodiment, the method 200 is used in combination with an embodiment of the method 100 wherein the interrogation signals are provided at successive different frequencies, each step 202, 208 of providing an interrogation signal 40 comprises providing a plurality of interrogations signals at successive decreasing or increasing frequencies.

In the drawings and specification, there have been disclosed preferred embodiments and examples of the invention and, although specific terms are employed, they are used in a generic and descriptive sense only and not for the purpose of limitation, the scope of the invention being set forth in the following claims.

The invention claimed is:

1. A system for detecting presence of liquid and/or humidity comprising:
   a sensor device for detection of liquid and/or humidity comprising a resonance circuit comprising an inductor connected to a capacitor, wherein:
   the capacitor comprises a first electrode and a second electrode together sandwiching at least a portion of a dielectric substrate,
   the first and second electrodes are configured to provide an overlap mismatch ($m_a$) relative to each other,
   the overlap mismatch area is at least 0.1% and less than 20% of the overlapping area ($o_a$) of the two electrodes, and
   the sensor device is arranged at a depth of 0.1-500 mm from an exposed surface of a structure to be analyzed; and
   a measuring unit comprising an inductive member and a controller, wherein the controller is configured to provide an interrogation signal to the inductive member and to receive a response signal from the inductive member.

2. The system according to claim 1, wherein one of the first and second electrodes provides a greater electrode area than the other one of the electrodes.

3. The system according to claim 1, wherein said dielectric substrate comprises a homogeneous material having a dielectric constant which is variable in response to liquid and/or humidity in its environment.

4. The system according to claim 1, wherein dielectric substrate comprises at least 70% by weight of a polymer selected from a group consisting of polyimides and polyethylene-tetrafluorides.

5. The system according to claim 1, wherein at least one of the first electrode and the second electrode is liquid permeable.

6. A method for detecting presence of liquid and/or humidity in a structure comprising:
   providing a sensor device for detection of liquid and/or humidity at a depth of 0.1-500 mm from an exposed surface of the structure,
   providing an interrogation signal to the sensor device by means of a controller and an inductive member in a measuring unit,
   receiving a response signal from the sensor device, and
   detecting the presence of liquid and/or humidity based on the response signal, wherein the sensor device is a sensor device for detection of liquid and/or humidity comprising a resonance circuit comprising an inductor connected to a capacitor,
   wherein the capacitor comprises a first electrode and a second electrode together sandwiching at least a portion of a dielectric substrate, and
   wherein the first and second electrodes are configured to provide an overlap mismatch ($m_a$) relative to each other, and
   wherein the overlap mismatch area is at least 0.1% and less than 20% of the overlapping area ($o_a$) of the two electrodes.

7. The method according to claim 6, wherein detecting the presence of liquid and/or humidity comprises associating the response signal with a detected liquid and/or humidity level.

8. The method according to claim 6, wherein detecting the presence of liquid and/or humidity comprises determining frequency of the response signal to associate said frequency with the detected liquid and/or humidity level.

9. The method according to claim 6, wherein providing the interrogation signal comprises providing the interrogation signal at a first power level, and determining whether the corresponding received response signal is within a predetermined power level range, and wherein the step of providing the interrogation signal comprises providing a plurality of interrogation signals at successively lower or higher interrogation signal power levels until a corresponding response signal is received which is within the predetermined response signal power level range.

10. A measuring unit comprising
a controller and at least one inductive member,
wherein the controller and the inductive member are configured to perform the steps of providing an interrogation signal and receiving a response signal in the method according to claim 6.

11. The method according to claim 6, wherein providing an interrogation signal comprises providing a plurality of interrogation signals at successively decreasing or increasing frequencies within a first frequency range and wherein receiving the response signal comprises receiving corresponding plurality of response signals.

12. The method according to claim 11, wherein determining the frequency of the response signal comprises comparing a response signal power level of a plurality of received response signals at different frequencies in said first frequency range, wherein the frequency of the response signal with the maximum signal power level is used for detecting the presence of liquid and/or humidity.

13. The method according to claim 11, wherein the plurality of interrogation signals is sent with a common phase, and wherein the phases of the plurality of received response signals are determined and used for detecting the presence of liquid and/or humidity.

14. The method according to claim 13, wherein a response signal, out of the plurality of received response signals, which is in phase or closest in phase with the sent interrogation signals, is used for detecting the presence of liquid and/or humidity.

15. A method for reading a passive wireless sensor device comprising a resonance circuit, the method comprising the steps of:
providing a wireless interrogation signal to the sensor device by means of an inductive member in a measuring unit,
receiving a response signal from the sensor device,
wherein the method further comprises a step of comparing power level of the received signal to a predetermined response signal power level range, and
wherein the step of providing the interrogation signal comprises providing a plurality of interrogation signals at successively decreasing or increasing signal power levels until a corresponding response signal is received which is determined to be within a predetermined response signal power level range, wherein the passive wireless sensor device is a sensor device for detection of liquid and/or humidity comprising
a resonance circuit comprising an inductor connected to a capacitor,
wherein the capacitor comprises a first electrode and a second electrode together sandwiching at least a portion of a dielectric substrate, and
wherein the first and second electrodes are configured to provide an overlap mismatch ($m_a$) relative to each other, and
wherein the overlap mismatch area is at least 0.1% and less than 20% of the overlapping area ($o_a$) of the two electrodes.

16. A measuring unit for reading a passive sensor configured to perform the method of claim 15.

* * * * *